(12) United States Patent
Mader et al.

(10) Patent No.: US 11,358,782 B2
(45) Date of Patent: Jun. 14, 2022

(54) CARTRIDGES, DISPENSERS, AND KITS FOR DISPENSING INSTRUMENT COVERS

(71) Applicant: Aseptiscope, Inc., San Diego, CA (US)

(72) Inventors: Scott W. Mader, San Diego, CA (US); Kelly M. Powers, San Diego, CA (US); W. Frank Peacock, San Diego, CA (US); Alan S. Maisel, San Diego, CA (US); Yuval Shenkal, San Diego, CA (US)

(73) Assignee: Aseptiscope, Inc., San Diego, CA (US)

( * ) Notice: Subject to any disclaimer, the term of this patent is extended or adjusted under 35 U.S.C. 154(b) by 0 days.

(21) Appl. No.: 17/163,224

(22) Filed: Jan. 29, 2021

(65) Prior Publication Data

US 2021/0221601 A1 Jul. 22, 2021

Related U.S. Application Data

(60) Continuation-in-part of application No. 16/865,182, filed on May 1, 2020, now abandoned, which is a
(Continued)

(51) Int. Cl.
*B65D 83/08* (2006.01)
*A61B 46/10* (2016.01)
(Continued)

(52) U.S. Cl.
CPC ............... *B65D 83/08* (2013.01); *A61B 7/02* (2013.01); *A61B 46/10* (2016.02); *A61B 50/20* (2016.02);
(Continued)

(58) Field of Classification Search
CPC ........ B65D 83/08; B65D 83/00; A61B 46/10; A61B 50/20; A61B 50/30; A61B 7/02;
(Continued)

(56) References Cited

U.S. PATENT DOCUMENTS 5,511,689 A * 4/1996 Frank .................... A61F 15/002
206/440
5,975,083 A * 11/1999 Henderson, Jr. ...... A41D 13/082
128/878

(Continued)

FOREIGN PATENT DOCUMENTS

EP 2595561 B1 * 6/2017 ............. A61B 90/70
KR 101109039 B1 * 2/2012 ........... B65H 37/005
(Continued)

*Primary Examiner* — Rakesh Kumar
(74) *Attorney, Agent, or Firm* — Lewis Kohn & Walker LLP; David M. Kohn

(57) ABSTRACT

A kit for dispensing disposable stethoscope covers and other instrument covers is provided. The kit may include a cartridge and a dispenser for automatic touch-free dispensing of disposable stethoscope covers. The kit further includes a first spool having a roll of backing member with disposable stethoscope covers disposed thereon and a second spool for receiving the spent backing member after a disposable stethoscope cover has been removed, self-contained within the cartridge. The cartridge is inserted within the dispenser so that a user may insert a stethoscope head through a window of the dispenser to attach to a disposable stethoscope cover. Alternatively, the cartridge or cassette may be comprised of disposable instrument covers so that a user may insert the instrument near or through the window of the dispenser for application of the instrument cover directly to the instrument. The kit may further include a proximity sensor for detecting a user.

15 Claims, 22 Drawing Sheets

Related U.S. Application Data division of application No. 15/853,555, filed on Dec. 22, 2017, now Pat. No. 10,676,270.

(60) Provisional application No. 62/438,390, filed on Dec. 22, 2016.

(51) Int. Cl.

| | | |
|---|---|---|
| *A61B 50/30* | (2016.01) | |
| *A61B 7/02* | (2006.01) | |
| *B65H 37/00* | (2006.01) | |
| *B65D 83/00* | (2006.01) | |
| *B65H 18/14* | (2006.01) | |
| *B65H 35/00* | (2006.01) | |
| *B65H 18/10* | (2006.01) | |
| *A61B 50/20* | (2016.01) | |
| *A61B 7/00* | (2006.01) | |

(52) U.S. Cl.
CPC .............. *A61B 50/30* (2016.02); *B65D 83/00* (2013.01); *B65H 18/10* (2013.01); *B65H 18/145* (2013.01); *B65H 35/006* (2013.01); *B65H 37/002* (2013.01); *A61B 7/00* (2013.01); *B65H 2405/421* (2013.01); *B65H 2511/512* (2013.01); *B65H 2553/23* (2013.01); *B65H 2553/40* (2013.01); *B65H 2701/1942* (2013.01)

(58) Field of Classification Search
CPC ........ B65H 18/00; B65H 83/00; B65H 18/10; B65H 18/145; B65H 35/006; B65H 37/002
USPC ......................... 422/28, 300; 221/9
See application file for complete search history.

(56) References Cited

U.S. PATENT DOCUMENTS

| | | | | |
|---|---|---|---|---|
| 6,018,835 | A * | 2/2000 | Schonfeld | B08B 3/02 |
| | | | | 15/97.1 |
| 6,206,134 | B1 * | 3/2001 | Stark | A61B 7/02 |
| | | | | 181/131 |
| 6,643,998 | B1 * | 11/2003 | Curtis | B65B 9/13 |
| | | | | 53/434 |
| 7,086,563 | B2 | 8/2006 | Maffei | |
| 7,117,971 | B1 * | 10/2006 | Cornacchia | A61B 7/02 |
| | | | | 221/266 |
| 9,486,287 | B2 | 11/2016 | Beebe | |
| 9,675,721 | B2 * | 6/2017 | Dayton | A61L 2/24 |
| 9,986,965 | B2 | 6/2018 | Fishberger | |
| 10,654,075 | B2 * | 5/2020 | Lesic | B08B 1/008 |
| 11,033,351 | B2 * | 6/2021 | Perlman | A61B 7/00 |
| 2005/0154491 | A1 | 7/2005 | Anderson et al. | |
| 2008/0257637 | A1 | 10/2008 | Miller et al. | |
| 2009/0125424 | A1 | 5/2009 | Wegelin | |
| 2010/0212995 | A1 * | 8/2010 | Hmayakyan | A61B 7/02 |
| | | | | 181/131 |
| 2011/0186590 | A1 * | 8/2011 | Lee | A61B 50/30 |
| | | | | 600/528 |
| 2012/0051969 | A1 * | 3/2012 | Nahman | A61B 7/02 |
| | | | | 422/28 |
| 2012/0261593 | A1 * | 10/2012 | Noori | A61L 2/10 |
| | | | | 250/492.1 |
| 2014/0124287 | A1 | 5/2014 | Fishberger | |
| 2015/0128997 | A1 * | 5/2015 | Lesic | A61B 7/00 |
| | | | | 15/210.1 |
| 2015/0136896 | A1 * | 5/2015 | Beebe | H05K 5/03 |
| | | | | 428/80 |
| 2016/0271659 | A1 | 9/2016 | Russ | |
| 2017/0258435 | A1 * | 9/2017 | Fishberger | A61B 7/02 |
| 2018/0201433 | A1 * | 7/2018 | Mader | B65D 83/08 |
| 2020/0138538 | A1 * | 5/2020 | Perlman | A61B 7/02 |

FOREIGN PATENT DOCUMENTS

| | | | | |
|---|---|---|---|---|
| KR | 20140030576 | A * | 3/2014 | ............ A61B 48/10 |
| KR | 20140030576 | A * | 12/2014 | ........... B65H 37/005 |
| WO | 2002081348 | | 10/2002 | |
| WO | WO-02081348 | A1 * | 10/2002 | ........... B65H 37/005 |
| WO | WO-2012010902 | A1 * | 1/2012 | ............ A61B 90/70 |
| WO | 2012141549 | | 10/2012 | |
| WO | WO-2012141549 | A2 * | 10/2012 | ............ A61B 46/10 |
| WO | WO-2012141549 | A3 * | 3/2013 | ............ A61B 46/10 |
| WO | 2014186362 | | 11/2014 | |
| WO | WO-2014186362 | A1 * | 11/2014 | ............ A61B 46/10 |

\* cited by examiner

CARTRIDGES, DISPENSERS, AND KITS FOR DISPENSING INSTRUMENT COVERS

RELATED APPLICATIONS

This application is a continuation-in-part claiming the benefit of priority from U.S. patent application Ser. No. 16/865,182, filed May 1, 2020, which claims the benefit of priority from U.S. patent application Ser. No. 15/853,555, filed on Dec. 22, 2017, now U.S. Pat. No. 10,676,270, which claims the benefit of priority from U.S. Provisional Patent Application No. 62/438,390, filed on Dec. 22, 2016, the disclosure of which is hereby incorporated by reference in its entirety.

FIELD OF THE INVENTION

This application generally relates to cartridges, dispensers, and kits for dispensing disposable stethoscope covers and ultrasound probe covers.

BACKGROUND OF THE INVENTION

A hospital-acquired infection (HAI), also known as a nosocomial infection, is an infection that is acquired in a hospital or other health care facilities. HAIs can be caused by bacteria, fungi, viruses, or other less common pathogens. These infections lead to the loss of tens of thousands of lives and cost the U.S. health care system billions of dollars each year. All hospitalized patients are susceptible to contracting a nosocomial infection. Some patients are at greater risk than others—young children, the elderly, and persons with compromised immune systems are more likely to get an infection. On any given day, about one in 25 hospital patients has at least one HAI.

The role of medical devices in the transmission of (HAIs) has long been recognize. With numerous studies demonstrating the transmission of pathogens from surface to patients and decades of medical literature chronicling stethoscope bacterial contamination rates to be consistently high (average of 85%), stethoscopes are considered to be a potentially significant vector for HAIs.

Although current standard of care guidelines recommends stethoscopes to be disinfected before and after each patient auscultation, it is generally recognized that most physicians and nurses do not disinfect their stethoscopes routinely. Survey and research data support this perception and reveal compliance to be less than 30%. Documented reasons for non-compliance include; current recommended practice is tedious and time consuming, supplies not available and/or not located within workflow, concerns about wear and tear on stethoscope, and lack of visual reminders. Addressing these issues is critical to developing an optimal solution that will be readily adopted by clinicians.

Disposable stethoscope covers provide a potential solution to protect against HAI. A stethoscope cover is a material that covers the surface of a stethoscope head, the portion of the stethoscope that comes into contact with the skin of a patient, and acts as a barrier to prevent the transfer of bacteria from the patient to the stethoscope, or vice versa. The disposables either cover or adhere to the stethoscope head for one-time use and may be discarded afterward. However, health care workers may still inadvertently forget to or purposefully avoid the hassle of using and/or replacing the stethoscope covers due to time constraints. Additionally, known storage devices for storing and dispensing disposable stethoscope covers all require manual activation, which may result in transmission of bacterial contamination from clinician's hands. For example, U.S. Pat. No. 7,117,971 to Cornacchia describes a stethoscope cover applicator for facilitating application of stethoscope covers. The applicator includes a base having a support surface, a cutting edge, and a spindle carrying a roll of a membrane for inhibiting contact between the stethoscope head and the patient during use. However, the applicator requires the health care worker to contact the stethoscope head with the membrane against the support surface, then manually unroll the spindle until the stethoscope and the attached membrane is past the cutting edge of the base, and subsequently apply pressure to tear the membrane via the cutting edge to separate the membrane attached to the stethoscope head and the rest of the membrane on the spindle.

Similarly, disposable covers for a variety of instruments is sorely lacking in the state of the art. Specifically, ultrasound probes have a great many shapes and sizes, making it difficult to develop a common set of parameters for a disposable probe cover that could be standardized across the market.

U.S. Patent Application No. 2011/0186590 to Lee describes a stethoscope cover and carrier strip assembly and a stethoscope cover dispenser. The dispenser requires a medical professional to manually advance a cover from a rolled carrier strip into a staging area where the cover is stretched in both a longitudinal and a lateral direction to allow unencumbered insertion of the stethoscope head. U.S. Patent Application No. 2008/0257637 to Miller describes a dispensing apparatus that places a disposable stethoscope head cover in an attachment station for attachment to a stethoscope head. The dispensing apparatus requires a dispensing arm to move a disposable cover from a pre-staging shelf into the attachment station. The dispensing apparatus may also determine when there are no disposable covers left in the pre-staging shelf when the dispensing arm is in a home position.

It would therefore be desirable to provide a touch-free stethoscope dispenser that may automatically dispense disposable stethoscope covers for attachment to a stethoscope head.

It would further be desirable to provide a touch-free stethoscope dispenser that may automatically alert a health care worker when the supply of disposable stethoscope covers is low or empty.

Additionally, there is a need in the art to provide a touch-free ultrasound probe dispenser that can automatically dispense disposable probe covers for attachment to an ultrasound probe.

SUMMARY OF THE INVENTION

The present disclosure overcomes the drawbacks of previously-known systems by providing cartridges, dispensers, and kits for dispensing disposable stethoscope covers. The kit may include a cartridge and a dispenser for receiving the cartridge. The cartridge may be disposable. The cartridge may include a first spool that holds a backing member having disposable stethoscope covers disposed thereon and a second spool that holds spent backing member without disposable stethoscope covers disposed thereon, such that the second spool is spaced apart from the first spool to define a flat area of the backing member disposed between the first and second spools, and wherein the flat area is sized to allow contact between a stethoscope head and the disposable stethoscope covers. In one embodiment, the cartridge may include a frame that spaces apart the second spool from the first spool, and a flat back element for maintaining the flat area of the backing member between the first and second spools.

The cartridge also includes a housing for containing the backing member having the disposable stethoscope covers disposed thereon and the spent backing member without disposable stethoscope covers disposed thereon. The housing may have a cartridge window for permitting the insertion of the stethoscope head therethrough to couple the stethoscope head to the disposable stethoscope cover exposed at the cartridge window and positioned at the flat area of the backing member. The housing may also have an opening on the backside for receiving a flat back element for maintaining the flat area of the backing member between the first and second spools. Additionally, the housing may include a protrusion that interacts with at least one of the first or second spools to prevent the first or second spools from unraveling. The first and second spools may rotate to expose the disposable stethoscope covers through the cartridge window. The dispenser is structured to receive the disposable cartridge, and may have a dispenser window aligned with the cartridge window and the exposed flat area of the backing member. In one embodiment, the dispenser may only be compatible with a cartridge having a specified marker, e.g., a physical marker, an electrical marker, or a barcode.

The kit may also include a motor and a processor having a memory and a communication chip. The processor may cause the motor to rotate the first and second spools. The processor and/or the motor may be disposed in either the cartridge or the dispenser. The processor may be operatively coupled to a proximity sensor that may detect when a user is in proximity to the dispenser window. Upon detection of a user, the processor causes the motor to rotate the first and second spools to expose the disposable stethoscope covers through the dispenser window. In one embodiment, the proximity sensor may not be activated until the cartridge is received in the dispenser. The memory may store acceptable user IDs such that the proximity sensor is not activated until a user ID reader operatively coupled to the processor detects an acceptable user ID. For example, acceptable user IDs may include a unique personal ID, a code, or an optical signature. Further, the memory may store information indicative of specific user usage based on the acceptable user IDs detected by the user ID reader. Additionally, the processor may be operatively coupled to a location sensor that detects a corresponding marker of the backing member adjacent each of the disposable stethoscope covers. The processor causes the motor to rotate the first and second spools until the location sensor detects the corresponding marker disposed on the backing member to align the disposable stethoscope covers with the dispenser window. The processor may also be operatively coupled an LED operatively coupled to the processor that lights up when the proximity sensor detects the user. The window of the dispenser may include a location ring that lights up when the LED lights up.

Each of the disposable stethoscope covers may include a unique target, such that the processor causes a target reader operatively coupled to the processor to detect the unique target and to store, in the memory, information indicative of a quantity of disposable stethoscope covers remaining on the first spool derived from the unique target. For example, the unique target may be a physical marker, an electrical marker, or a barcode. The target reader may also detect when the disposable stethoscope covers are removed from the flat area of the backing member, such that the processor causes the proximity sensor to delay from detecting another user for a time period after the target reader detects that one of the disposable stethoscope covers has been removed. The memory may also store a disposable stethoscope cover threshold, such that the processor generates an alert, e.g., a visual alert, when the quantity of disposable stethoscope covers remaining on the first spool approaches or reaches the disposable stethoscope cover threshold. The processor may also transmit stored data to a remote storage via the communication chip.

In accordance with yet another aspect of the present disclosure, an automatic touch-free disposable stethoscope cover dispensing system is described. The system may include a first spool that holds a backing member having disposable stethoscope covers disposed thereon and a second spool that holds spent backing member without disposable stethoscope covers disposed thereon, such that the second spool is spaced apart from the first spool to define a flat area of the backing member disposed between the first and second spools, and wherein the flat area is sized to allow contact between a stethoscope head and the disposable stethoscope covers. The system also includes a cartridge for housing the backing member having the disposable stethoscope covers disposed thereon and the spent backing member without disposable stethoscope covers disposed thereon. The cartridge includes a cartridge window for permitting insertion of the stethoscope head therethrough to couple the stethoscope head to the disposable stethoscope cover exposed at the cartridge window and positioned at the flat area of the backing member. The system also includes a dispenser for receiving the cartridge. The dispenser may have a dispenser window aligned with the cartridge window and the exposed flat area of the backing member, such that the first and second spools rotate to align the disposable stethoscope covers with the dispenser window.

In another aspect, the present invention provides for a kit comprising a dispenser and a cassette for automatic touch-free dispensing of disposable instrument covers, the cassette comprising: a first spool configured to hold a backing member having the disposable instrument covers disposed thereon; a second spool configured to hold spent backing members without the disposable instrument covers disposed thereon, the second spool spaced apart from the first spool to define a flat area of the backing member disposed between the first and second spools, the flat area sized to allow contact between an instrument and the disposable instrument covers; and a dispenser housing with a lid configured to house the cartridge, the dispenser housing comprising a cartridge window configured to permit insertion of the instrument therethrough to permit coupling of the instrument to the disposable instrument cover exposed at the cartridge window and positioned at the flat area of the backing member, wherein the first and second spools are configured to rotate such that the disposable instrument covers are exposed through the cartridge window. Preferably, the dispenser housing comprises a dispenser window aligned with the cartridge window and the exposed flat area of the backing member. Most preferably, the instrument is an ultrasound probe and the disposable instrument covers are disposable covers for application to the ultrasound probe.

In another aspect, the present invention provides for a cassette for automatic touch-free dispensing of disposable instrument covers onto an instrument, the cassette comprising: a first spool configured to hold a backing member having the disposable instrument covers disposed thereon; a second spool configured to hold spent backing members without the disposable instrument covers disposed thereon, the second spool spaced apart from the first spool to define a flat area of the backing member disposed between the first and second spools; and a peeler pin positioned proximate to the first spool and used to partially separate the disposable instrument covers from the backing member to ease the transfer of the disposable instrument cover onto the instrument, wherein the first and second spools are configured to rotate such that the disposable instrument covers are exposed through a cassette window positioned at a front face of the cassette. Preferably, the flat area comprises a resistance section which provides resistance to the backing member once the disposable instrument contacts the disposable instrument cover through the cassette window.

The present invention further provides for an aspect wherein the cassette comprises a lid further comprising separate spool structures to interface with the first spool and the second spool within the cassette. Optionally, the cassette comprises a cassette flooring through which at least a drive port and a supply port are positioned. Preferably, the present invention provides for a drive gear connected to a motor that extends through the cassette flooring at the drive port to interface with the first spool or the second spool. Most preferably, the drive port is positioned below the second spool and the supply port is positioned below the first spool.

Optionally, the present invention further provides for the flat area sized to allow contact between an instrument and the disposable instrument covers. Most preferably, the instrument is an ultrasound probe.

In yet another aspect, the present invention provides for a kit comprising a dispenser and a cassette for automatic touch-free dispensing of disposable instrument covers onto an instrument, the cassette comprising: a first spool configured to hold a backing member having the disposable instrument covers disposed thereon; a second spool configured to hold spent backing members without the disposable instrument covers disposed thereon, the second spool spaced apart from the first spool to define a flat area of the backing member disposed between the first and second spools, wherein the first and second spools are configured to rotate such that the disposable instrument covers are exposed through a cassette window positioned at a front face of the cassette; a peeler pin positioned proximate to the first spool and used to partially separate the disposable instrument covers from the backing member to ease the transfer of the disposable instrument cover onto the instrument; and a dispenser housing with a lid configured to house the cassette, the dispenser housing comprising an access window configured to permit insertion of the instrument therethrough to permit coupling of the instrument to the disposable instrument cover exposed at the access window and positioned at the flat area of the backing member, wherein the first and second spools are configured to rotate such that the disposable instrument covers are exposed through the access window. Preferably, the cassette window of the cassette and the access window of the dispenser housing are aligned.

Most preferably, this aspect of the present invention provides for the flat area further comprising a resistance section which provides resistance to the backing member once the disposable instrument contacts the disposable instrument cover through the cassette window. Optionally, the cassette comprises a lid further comprising separate spool structures to interface with the first spool and the second spool within the cassette. Alternatively, the cassette comprises a cassette flooring through which at least a drive port and a supply port are positioned. In a preferred embodiment, a drive gear is connected to a motor and extends through the cassette flooring at the drive port to interface with the first spool or the second spool. In a most preferred embodiment, the drive port is positioned below the second spool and the supply port is positioned below the first spool.

Preferably, the flat area is sized to allow contact between an instrument and the disposable instrument covers. Most preferably, the instrument is an ultrasound probe and the disposable instrument covers are disposable covers for application to the ultrasound probe.

DETAILED DESCRIPTION OF THE INVENTION

The kit for dispensing disposable stethoscope covers comprises a cartridge having a spool of backing member with disposable stethoscope covers disposed thereon and a spool for collecting spent backing member, self-contained therein, and a dispenser for receiving the cartridge and for touch-free dispensing of the disposable stethoscope covers. The kit further includes a power source for powering a motor to dispense the disposable stethoscope covers. In accordance with the principles of the present disclosure, the kit disclosed herein may be utilized for automatic touch-free dispensing of disposable stethoscope covers.

Referring to FIGS. 1A-1D, an exemplary cartridge of a kit for dispensing disposable stethoscope covers constructed in accordance with the principles of the present disclosure is described. Cartridge 100 comprises cartridge housing 110, first spool 102, second spool 104, backing member 106, and disposable stethoscope covers. First spool 102, second spool 104, backing member 106, and the disposable stethoscope covers are sized and shaped to be self-contained within cartridge housing 110 such that backing member 106 transfers from first spool 102 to second spool 104, entirely within cartridge housing 110.

Figure 1A:
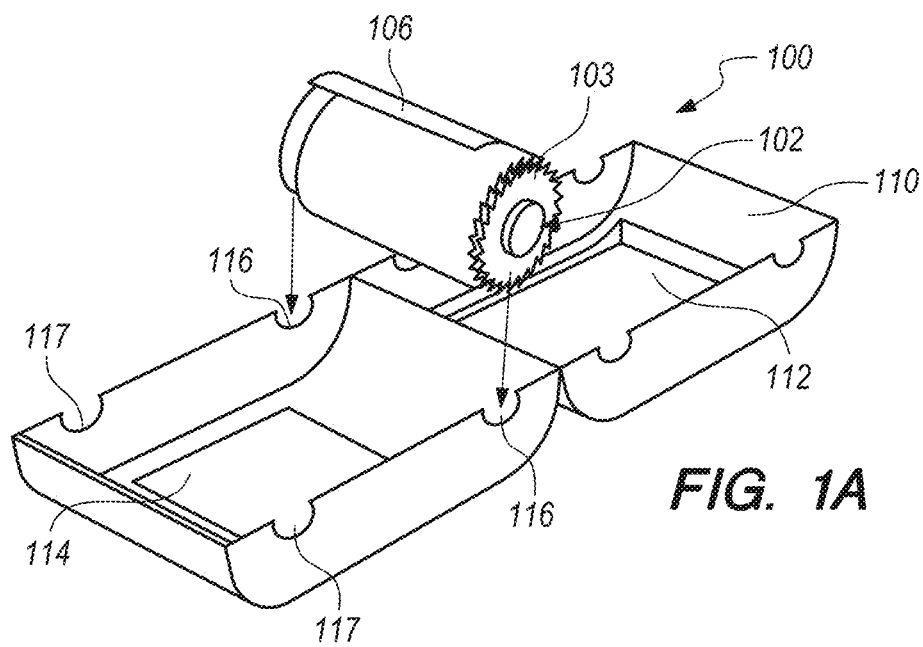
FIGS. 1A through 1D show an exemplary cartridge of a kit for dispensing disposable stethoscope covers constructed in accordance with the principles of the present disclosure.

As shown in FIG. 1A, cartridge housing 110 comprises cartridge window 112, back opening 114, first spool notches 116, and second spool notches 117. Cartridge opening 112 is sized to permit exposure of backing member 106 and the disposable stethoscope covers disposed thereon from within housing 110 such that the disposable stethoscope covers may be attached to a stethoscope head. Back opening 114 is sized to allow a back element having a flat surface enter cartridge 100 to press against the backside of a portion of backing member 106 to thereby provide a flat area of backing member 106 such that a stethoscope head may press against the flat area of backing member 106, e.g., touch-free, to attach to the disposable stethoscope cover disposed thereon. First spool notches 116 are sized and shaped to engage with the opposite ends of first spool 102 and second spool notches 117 are sized and shaped to engage with the opposite ends of second spool 104. As shown in FIG. 1A, first spool 102 may have a full roll of backing member 106 disposed thereon. Preferably, a full roll of backing member 106 may comprise up to, for example, 250, 500, or 1000 disposable stethoscope covers. The disposable stethoscope covers may be equally spaced apart on backing member 106.

The disposable stethoscope covers may be constructed similar to those well known in the art. For example, U.S. Pat. No. 5,686,706 to Wurzburger, the entire disclosure of which is incorporated by reference herein, describes disposable stethoscope covers removably attachable to a stethoscope head. As described in Wurzburger, the disposable stethoscope covers may include an appendage for easy removal of the cover from the stethoscope head after use. The disposable stethoscope covers may be removably affixed to backing member 106 on one side via, e.g., an adhesive backing, such that the disposable stethoscope covers are disposed on backing member 106 when rolled about the central axis of first spool 102. The disposable stethoscope covers may be made of a thin flexible material having antimicrobial properties for ease of attachment and removal to and from backing member 106. Other material compositions of the disposable stethoscope covers may be used as will be understood by one skilled in the art.

As shown in FIG. 1A, first spool 102 may be contained within housing 110 by engaging the opposite ends of first spool 102 within first spool notches 116. At least one of the ends of first spool 102 may comprise sprocket 103 as described in more detail below. As one skilled in the art would understand, the ends of first spool 102 may have a diameter larger than the diameter of the center axis of first spool 102 such that a roll of backing member 106 may be contained in between the ends of first spool 102.

Figure 1B:
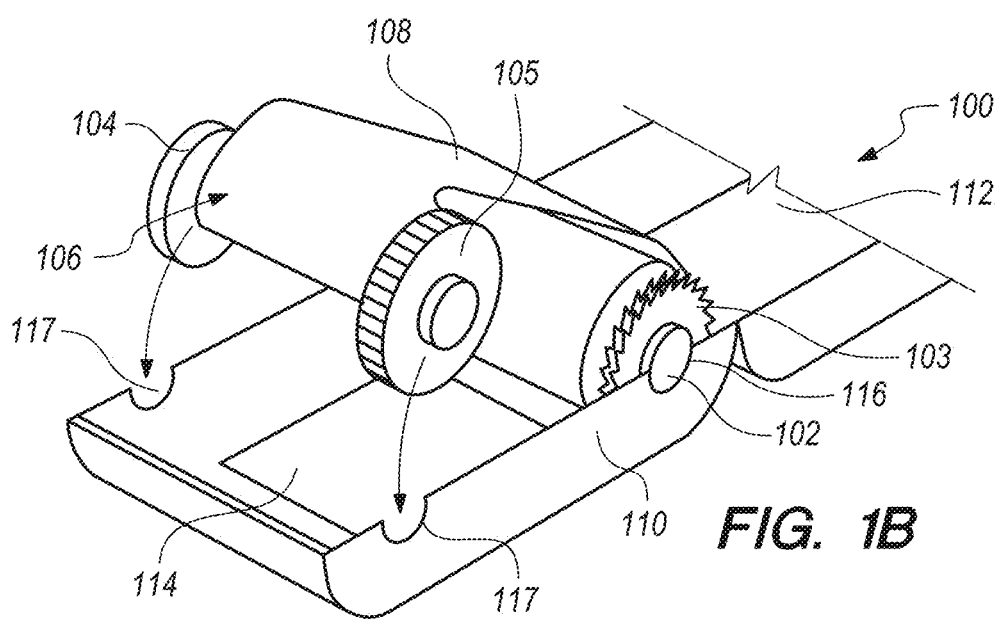

As shown in FIG. 1B, a portion of backing member 106 may be pulled from the roll of backing member 106 disposed on first spool 102 and wrapped around and affixed to the center axis of second spool 104. A portion of backing member 106 disposed between first spool 102 and second spool 104 forms flat area 108. Second spool 104 may be contained within housing 110 by engaging the opposite ends of second spool 104 within second spool notches 117, such that flat area 108 is positioned above back opening 114 of housing 110. At least one of the ends of second spool 104 may comprise spool gear 105 as described in more detail below. As one skilled in the art would understand, the ends of second spool 104 may have a diameter larger than the diameter of the center axis of second spool 104 such that a roll of spent backing member 106 may be contained in between the ends of second spool 104.

Figure 1C:
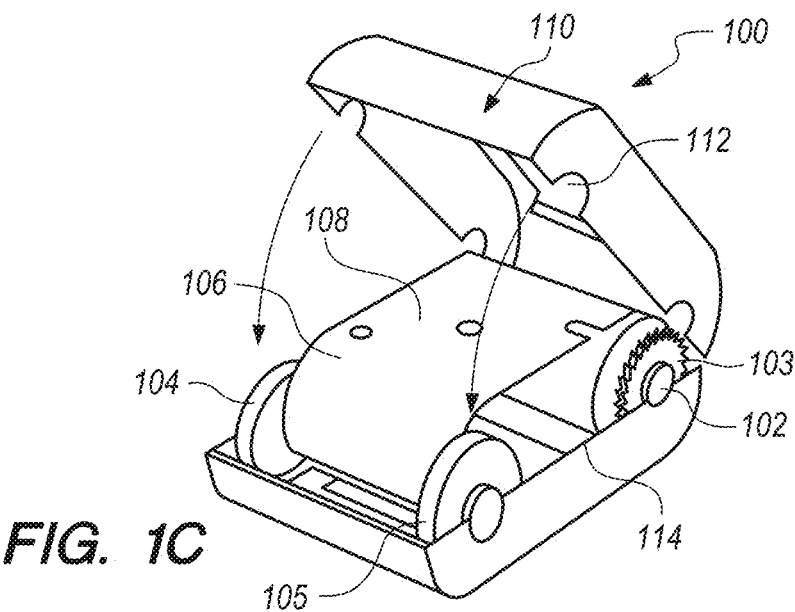

FIG. 1C illustrates cartridge 100 wherein first spool 102 and second spool 104 are both engaged with housing 110. As shown in FIG. 1C, housing 110 may transition from an open configuration to a closed configuration wherein first spool 102, second spool 104, backing member 106, and the disposable stethoscope covers are self-contained within housing 110.

Figure 1D:
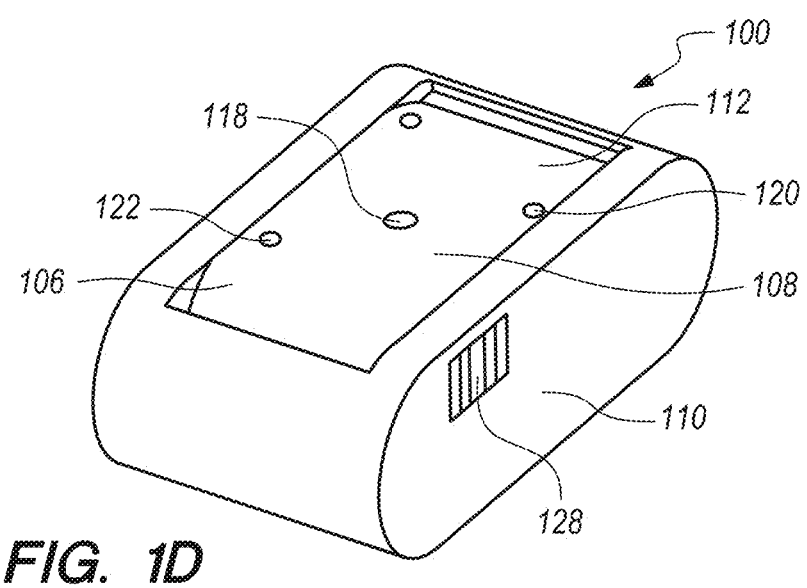

FIG. 1D illustrates cartridge 100 wherein housing 110 is in the closed configuration such that first spool 102, second spool 104, backing member 106, and the disposable stethoscope covers are self-contained within housing 110. As shown in FIG. 1D, flat area 108 of backing member 106 is exposed through cartridge window 112. The portion of backing membrane 106 forming flat area 108 in FIG. 1D is shown without a disposable stethoscope cover in a ready-to-dispense position. In one embodiment, backing member 106 may comprise proximity sensor hole 118, marker 120, and LED hole 122, in proximity to the location of each disposable stethoscope cover disposed on backing member 106, described in more detail below. As shown in FIG. 1D, cartridge housing 110 may further include specified marker 128, e.g., physical marker, electrical marker, or barcode, such that a dispenser designed to receive cartridge 100 will only be compatible with cartridges having the specified marker as described in further detail below.

Figure 2:
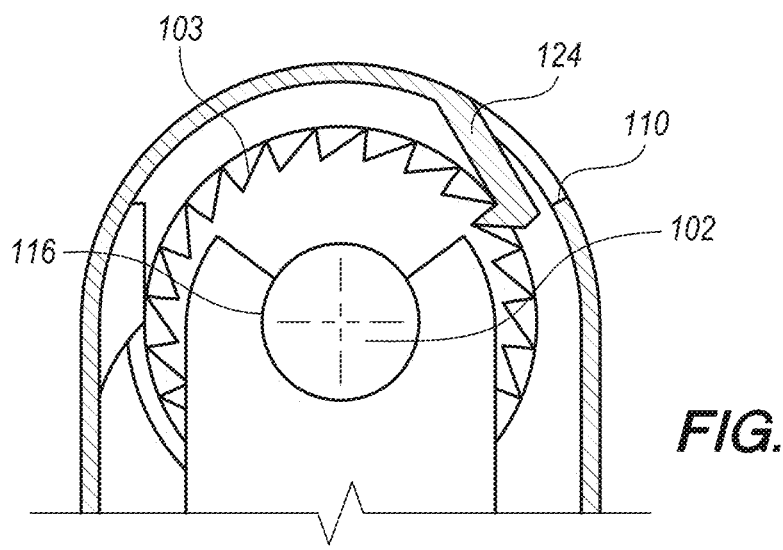
FIG. 2 shows an embodiment of the present disclosure wherein the spool includes a sprocket.

As shown in FIG. 2, at least one end of first spool 102 may comprise sprocket 103. Sprocket 103 comprises a series of protrusions around the circumferential edge of an end of first spool 102. Housing 110 may include protrusion 124 that engages with the series of protrusions of sprocket 103 when first spool 102 is engaged with first spool notches 116 to permit first spool 102 to rotate unidirectionally toward second spool 104, e.g., counter-clockwise, and prevent the roll of backing member 106 from unraveling within housing 110.

Figure 3A:
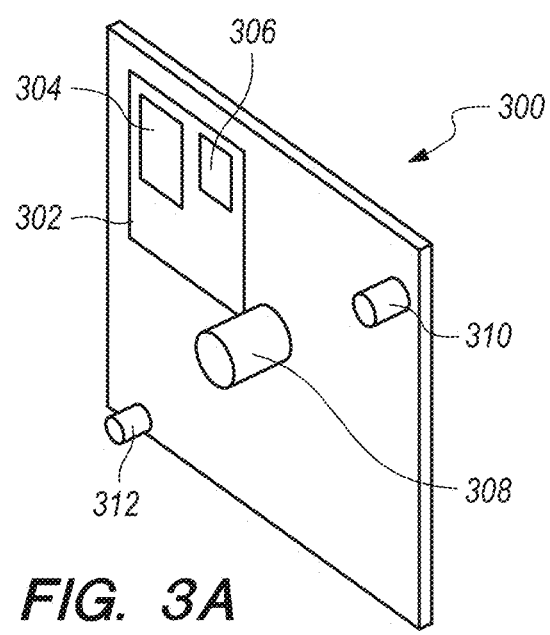
FIG. 3A shows an exemplary printed circuit board of a kit for dispensing disposable stethoscope covers constructed in accordance with the principles of the present disclosure.

Referring to FIG. 3A, an exemplary printed circuit board (PCB) of a kit for dispensing disposable stethoscope covers constructed in accordance with the principles of the present disclosure is described. As shown in FIG. 3A, PCB 300 comprises processor 302 having memory 304 and communication chip 306, proximity sensor 308, location sensor 310, and LED 312 (optional). In FIG. 3A, components of processor 302 are not depicted to scale on either a relative or absolute basis. Processor 302 may be operatively coupled to proximity sensor 308, location sensor 310, and LED 312.

Proximity sensor 308 may be any sensor known in the art to detect when a user is within a predetermined proximity. Proximity sensor 308 may begin detecting for users upon activation of proximity sensor 308 by processor 302. Upon detection of a user within a predetermined proximity, processor 302 may cause first spool 102 and second spool 104 to rotate such that a portion of backing member 106 travels from first spool 102 to second spool 104. Backing member 106 may continuously travel from first spool 102 to second spool 104 until location sensor 310 detects marker 120 disposed on backing member 106 adjacent to each disposable stethoscope cover. Marker 120 may be, for example, a digital, physical, or electronic marker. Upon detection of marker 120 by location sensor 310, processor 302 causes first spool 102 and second 104 to stop rotating. Marker 120 will be located at a position on backing member 106 such that when backing member 106 stops traveling from first spool 102 to second spool 104, a subsequent portion of backing member 106 forms flat area 108 having a disposable stethoscope cover in a ready-to-dispense position such that the disposable stethoscope cover is aligned with cartridge window 112.

Figure 3B:
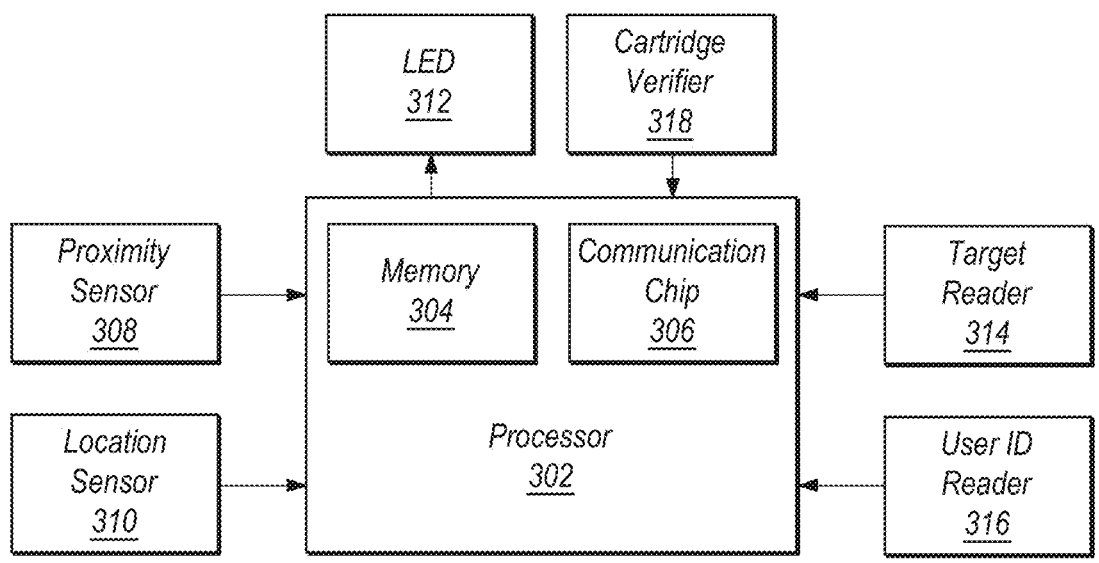
FIG. 3B is a schematic illustration of various components operatively coupled to a processor constructed in accordance with the principles of the present disclosure.

Referring to FIG. 3B, various components operatively coupled, e.g., by electrical connection, to processor 302 in accordance with the principles of the present disclosure are described. As shown in FIG. 3B, processor 302 may be operatively coupled to target reader 314, e.g., an optical sensor, user ID reader 316, and cartridge verifier 318. Accordingly, each disposable stethoscope cover disposed on backing member 106 may include a unique target. Each unique target may have information embedded therein indicative a quantity of disposable stethoscope covers remaining on the roll of backing member 106 disposed on first spool 102. Each unique target may be, for example, a physical marker such as a number or a color, an electrical marker, or a barcode, such that target reader 314 may detect the unique target. Target reader 314 may be mounted within housing 110 or within a dispenser as described in further detail below. When a disposable stethoscope cover is aligned with cartridge window 112 in a ready-to-dispense position, processor 302 may cause target reader 314 to detect the unique target and to store, in memory 304, information indicative of a quantity of disposable stethoscope covers remaining on first spool 102 derived from the unique target. Target reader 314 may also detect the presence of a disposable stethoscope cover on backing member 106. Upon detection of the removal of the disposable stethoscope cover from flat area 108 of backing member 106, processor 302 may delay reactivation of proximity sensor 308 for a predetermined amount of time, e.g., 3, 5, or 10 seconds. For example, after target reader 314 detects that a disposable stethoscope cover has been removed from flat area 108 of backing member 106, proximity sensor 308 will not detect a user, and accordingly will not cause rotation of first spool 102 and second spool 104, until the predetermined amount of time has elapsed.

Memory 304 may store a disposable stethoscope cover threshold such that processor 302 compares the quantity of disposable stethoscope covers remaining on first spool 102 against the disposable stethoscope cover threshold, and generates an alert when the quantity of disposable stethoscope covers remaining on first spool approaches and/or reaches the disposable stethoscope cover threshold. The alert may be a signal generated by processor 302 and transmitted to a remote, external computing device or external storage, e.g., mobile phone, laptop, computer, or Cloud, via communication chip 306 such that a person using or observing the external computing device or uploading data from the external storage may be notified that disposable cartridge 100 is low and/or needs to be replaced. Communication chip 306 may transmit and receive data via, e.g., Bluetooth, Wi-Fi, or cellular communication. Additionally, or alternatively, the alert may be a light signal produced by LED 312. For example, LED 312, aligned with LED hole 122, may light up yellow to indicate that the supply of disposable stethoscope covers is approaching the disposable stethoscope cover threshold by a predetermined amount, and/or red to indicate that the supply of disposable stethoscope covers has reached the disposable stethoscope cover threshold.

The subsequent portion of backing member 106 that travels from first spool 102 to form flat area 108 will have a disposable stethoscope cover disposed thereon as described above. In one embodiment, proximity sensor 308 may be aligned with proximity sensor hole 118 of backing member 106, and may also detect the presence of a disposable stethoscope cover on backing member 106. Upon detection of the removal of the disposable stethoscope cover from flat area 108 of backing member 106, processor 302 may delay reactivation of proximity sensor 308 for a predetermined amount of time, e.g., 3, 5, or 10 seconds. For example, after proximity sensor 308 detects that a disposable stethoscope cover has been removed from flat area 108 of backing member 106, proximity sensor 308 will not detect a user, and accordingly will not cause rotation of first spool 102 and second spool 104, until the predetermined amount of time has elapsed.

Memory 304 may store acceptable user IDs that correspond to user IDs assigned to various users. Accordingly, user ID reader 316 may detect the user IDs assigned to various users such that processor 302 does not activate proximity sensor 308 until a user ID is detected which matches an acceptable user ID stored in memory 304. The user ID assigned to the various users may be, for example, a unique personal ID, a scan card having a barcode, a passcode, or an optical signature. User ID reader 316 may be any well-known device for detecting a user ID, for example, a barcode scanner having a light source, a lens, and a light sensor for translating optical impulses into electric impulses to detect a barcode, or a graphical user interface (GUI) for receiving a passcode. Memory 304 may further store information indicative of usage by the various users to track specific user usage based on the acceptable user IDs detected by user ID reader 316.

As described above, each cartridge housing 110 may further include specified marker 128, e.g., physical marker, electrical marker, or barcode, such that a dispenser designed to receive cartridge 100 will only be compatible with cartridges having the specified marker. Accordingly, cartridge verifier 318 may detect the specified marker disposed on cartridge housing 110 such that processor 302 does not activate proximity sensor 308 until the specified marker is detected. Cartridge verifier 318 may be any well-known device for detecting a specified marker, for example, a bar code scanner or an optical sensor. Cartridge verifier 318 may be mounted within the dispenser as described in further detail below.

Figure 3C:
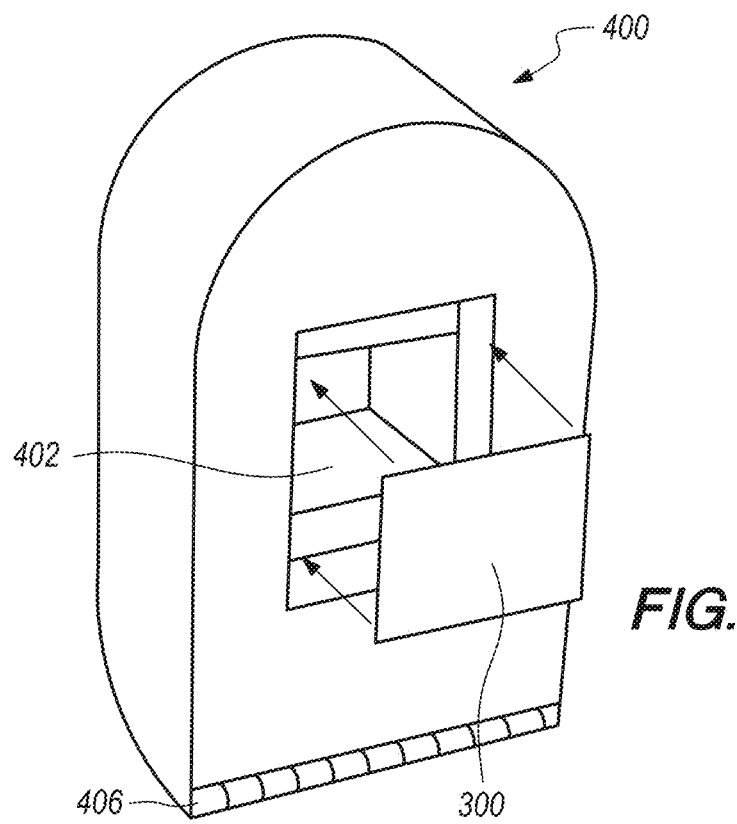
FIG. 3C illustrates the insertion of the printed circuit board of FIG. 3A into a dispenser for receiving the cartridge of FIGS. 1A through 1D and for dispensing disposable stethoscope covers.

As show in FIG. 3C, PCB 300 may be positioned within back element 402 of dispenser 400. As described above, back element 402 is a portion of dispenser 400 having a flat surface that may enter cartridge 100 through back opening 114 of housing 110 to press against the backside of a portion of backing member 106 to thereby provide flat area 108 of backing member 106 such that a stethoscope head may press against flat area 108 of backing member 106, e.g., touch-free, to attach to the disposable stethoscope cover disposed thereon. PCB 300 may be positioned within back element 402 such that proximity sensor 308, location sensor 310, and LED 312 aligns with a proximity sensor hole, location sensor hole, and LED hole, respectively, of back element 402 as described in more detailed below.

Figure 4A:
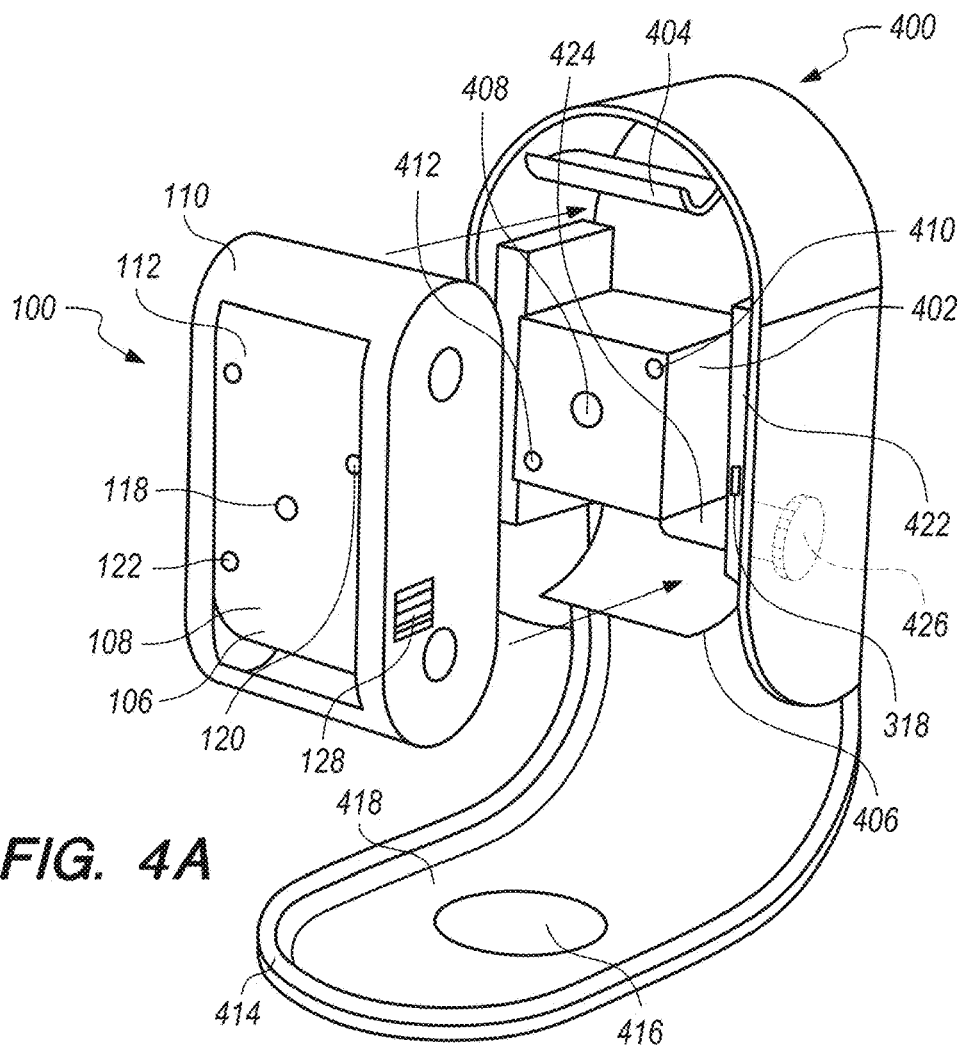
FIG. 4A illustrates the insertion of the cartridge of FIGS. 1A through 1D into an exemplary dispenser for dispensing disposable stethoscope covers constructed in accordance with the principles of the present disclosure.

Referring now to FIGS. 4A through 4D, the insertion of cartridge 100 into an exemplary dispenser for dispensing disposable stethoscope covers constructed in accordance with the principles of the present disclosure is described. As shown in FIG. 4A, dispenser 400 comprises front panel 414 having dispenser window 416 and location ring 418, wherein front panel 414 may pivot about dispenser hinge 406 such that dispenser 400 may transition between an open configuration and a closed configuration. Dispenser 400 is designed to be easily cleaned, e.g., rounded edges, and may be wall-mounted to hold the cartridge in a readily accessible orientation and position. Dispenser 400 may further include back element 402 having proximity sensor hole 408, location sensor hole 410, and LED hole 412, which aligns with proximity sensor 308, location sensor 310, and LED 312, respectively, of PCB 300 positioned within back element 402, and cartridge clamp 404 for removably securing cartridge 100 within dispenser 400. When cartridge 100 is fully inserted within dispenser 400, proximity sensor 308, location sensor 310, and LED 312 of PCB 300 are aligned with proximity sensor hole 408, location sensor hole 410, and LED hole 412, respectively, of back element 402, and with proximity sensor hole 118, marker 120, and LED hole 122, respectively, of backing member 106. As described above, dispenser 400 may include cartridge verifier 318 such that dispenser 400 will only be compatible with cartridges having specified marker 128, e.g., physical marker, electrical marker, or barcode.

Dispenser 400 may house power source 422, motor 424, and dispenser gear 426, wherein motor 422 is operatively coupled to processor 302. When cartridge 100 is fully inserted within dispenser 400, spool gear 105 of second spool 104 engages with dispenser gear 426 through an opening of cartridge housing 110 of cartridge 110. As described above, upon detection of a user by proximity sensor 308, processor 302 may cause motor 424 to rotate gear 426 which causes the rotation of spool gear 105 and accordingly second spool 104. The rotation of second spool 104 causes backing member 106 to travel from first spool 102 to second spool 104. Therefore, as a disposable stethoscope cover is removed from backing member 106, the spent backing member is collected by second spool 104 and self-contained within housing 110. Power source 422 delivers power to the components of PCB 300 and to motor 424 to rotate dispenser gear 426. Power source 422, e.g., battery, may have an amount of energy stored equal to the dispensing power required to dispense a full roll of disposable stethoscope covers, e.g., up to 250, 500, or 1000 covers.

Figure 4B:
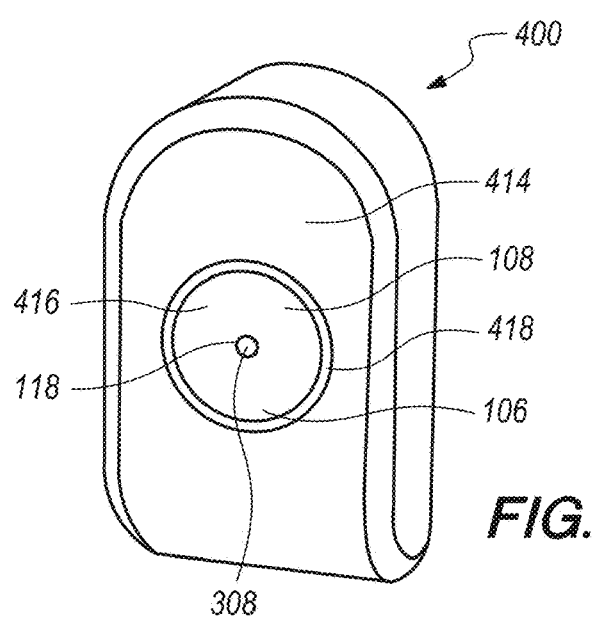
FIG. 4B shows the dispenser of FIG. 4A in a closed configuration.

FIG. 4B illustrates dispenser 400 in a closed configuration with cartridge 100 disposed therein. As shown in FIG. 4B, flat area 108 of backing member 106 is aligned with and exposed through dispenser window 416. Additionally, proximity sensor 308 is aligned with proximity sensor hole 408 of back element 402 and proximity sensor hole 118 of backing member 106. Location ring 418 may encircle dispenser opening 416 and may be adjacent to LED 112 when dispenser 400 is in a closed configuration. Location ring 418 may be composed of a translucent material such that location ring 418 illuminates when LED 312 lights up. In one embodiment, LED 312, aligned with LED hole 122, may illuminate a light, e.g., white, green, or blue, constantly while proximity sensor 308 is activated, causing location ring 418 to illuminate in a similar manner. This may be helpful in parts of the hospital that may be dark, such as an operating room, so the health care worker may locate dispenser window 416 and know where to place the stethoscope head to attach to a disposable stethoscope cover. As described above, the color of the light illuminated by LED 312, and accordingly location ring 418, may change depending on the quantity of disposable stethoscope covers remaining in cartridge 100.

Figure 4C:
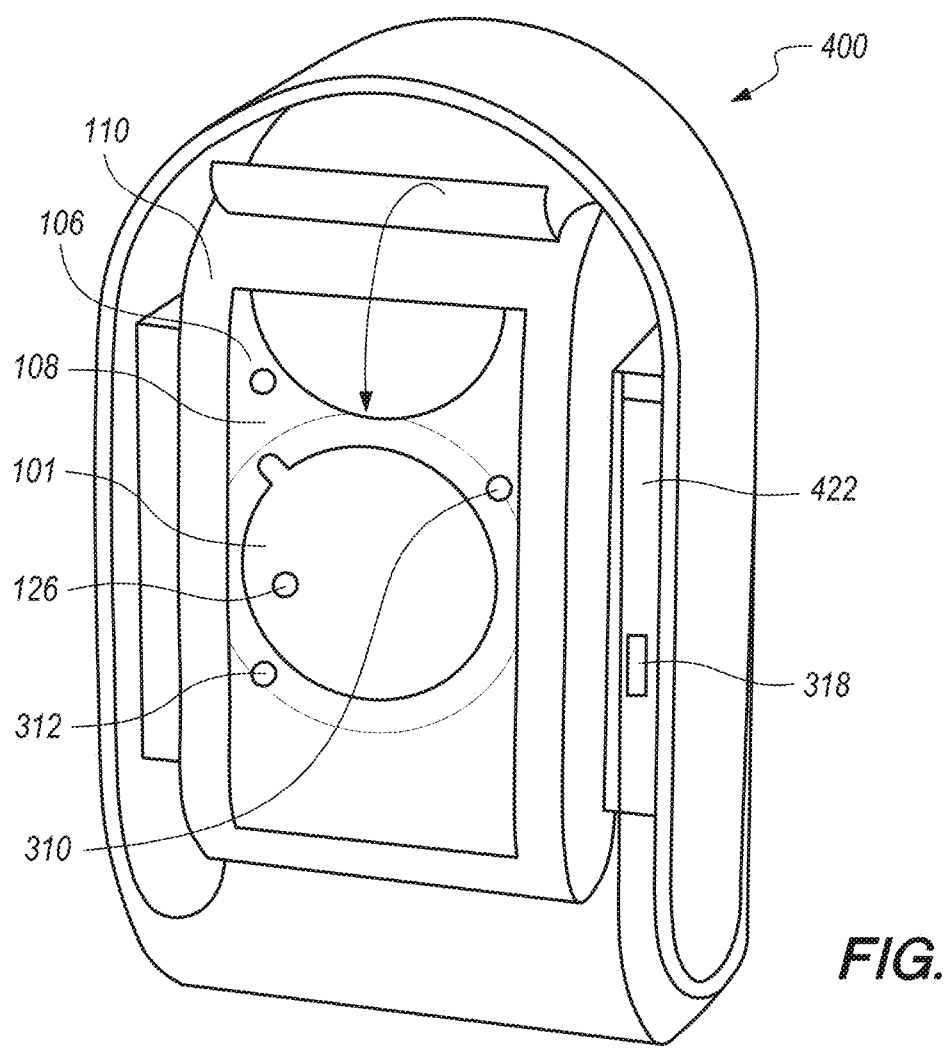
FIG. 4C shows the interior of the dispenser of FIG. 4A in a closed configuration with a disposable stethoscope cover aligned with the dispenser window.

FIG. 4C illustrates the interior of dispenser 400 in a closed configuration with cartridge 100 disposed therein wherein a disposable stethoscope cover is in a ready-to-dispense position. As shown in FIG. 4C, disposable stethoscope cover 101 is disposed on flat area 108 of backing member 106 between first spool 102 and second spool 104 within housing 110 of cartridge 100. Disposable stethoscope cover 101 was moved into the ready-to-dispense position upon proximity sensor 308 detecting a user, and processor 302 causing second spool 104 to rotate via motor 424 and gear 426 until location sensor 310 detected marker 120 on backing member 106 adjacent to disposable stethoscope cover 101. As described above, disposable stethoscope cover 101 may include unique target 126 having information indicative of a quantity of disposable stethoscope covers remaining on first spool 102 embedded therein, such that memory 304 may store the information upon the detection of unique target 126 by target reader 314.

Figure 4D:
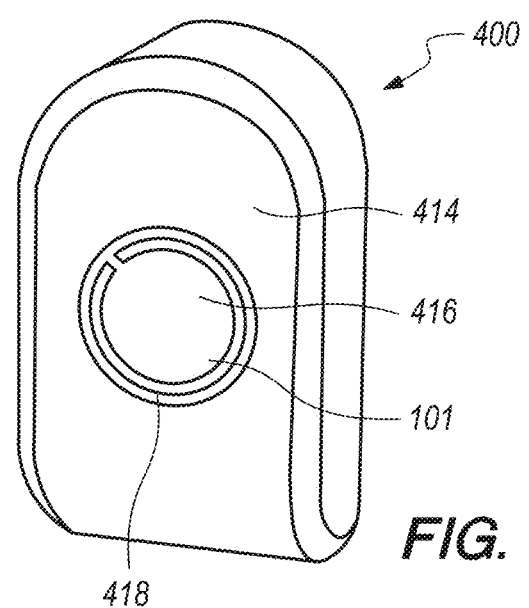
FIG. 4D is an exterior view of the dispenser of FIG. 4C.

FIG. 4D illustrates dispenser 400 having disposable stethoscope cover 101 aligned with dispenser window 418, ready for a user, e.g., health care worker, to position a stethoscope head within dispenser window 416 to contact and adhere to disposable stethoscope cover 101, and to remove disposable stethoscope cover 101 from flat area 108 of backing member 106. As described above, after target reader 314 or proximity sensor 308 detects that disposable stethoscope cover 101 has been removed from backing member 106, processor 302 may delay reactivation of proximity sensor 308. After a predetermined amount of time, proximity sensor 308 may be reactivated such that proximity sensor 308 is able detect a user, permitting a subsequent disposable stethoscope cover to be moved to the ready-to-dispense position. As described above, location ring 418 may communicate to a user the quantity of disposable stethoscope covers remaining in cartridge 100. Accordingly, when cartridge 100 is ready to be replaced, front panel 414 of dispenser 400 may transitioned to an open configuration so that empty cartridge 100 may be removed from dispenser 400 by disengaging empty cartridge 100 from cartridge clamp 404 within dispenser 400, and a full cartridge may be inserted into dispenser 400. As described above, PCB 300, power source 422, motor 424, and gear 426 may be disposed within dispenser 400. However, in an alternative embodiment, the PCB, power source, motor, and gear may be fully contained within a disposable cartridge, such that the dispenser only holds the cartridge in a readily accessible orientation and position, as described in further detail below.

Figure 5A:
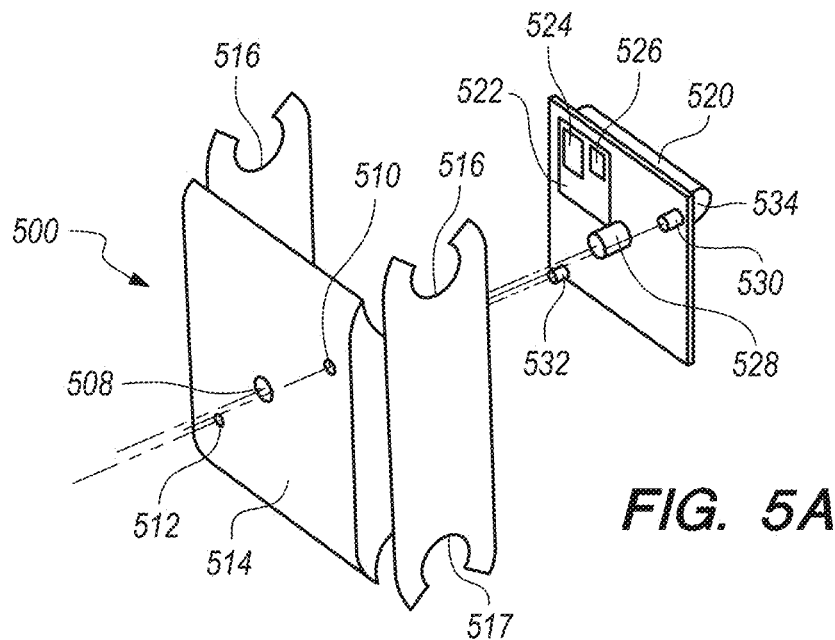
FIGS. 5A through 5D show an exemplary spool frame of a kit for dispensing disposable stethoscope covers constructed in accordance with the principles of the present disclosure.

Referring to FIGS. 5A through 5D, an exemplary spool frame of a kit for dispensing disposable stethoscope covers constructed in accordance with the principles of the present disclosure is described. Spool frame 500 comprises flat back portion 514, first spool 502, second spool 504, backing member 506, power source 534, motor 509, frame gear 507, and PCB 520. First spool 502 and second spool 504 are constructed similarly to first spool 102 and second spool 104, respectively, of FIGS. 1A-1D, such that sprocket 503 and spool gear 505 correspond to sprocket 103 and spool gear 105. As shown in FIG. 5A, flat back portion 514 is fixed to two frame arms, each having first spool notch 516 and second spool notch 517. Flat back portion 514 allows the backside of a portion of backing member 506 between first spool 502 and second spool 504 to rest against flat back portion 514 to thereby provide a flat area of backing member 506 such that a stethoscope head may press against the flat area of backing member 506, e.g., touch-free, to attach to the disposable stethoscope cover disposed thereon. First spool notches 516 are sized and shaped to engage with the opposite ends of first spool 502 and second spool notches 517 are sized and shaped to engage with the opposite ends of second spool 504. Flat back portion 514 may include proximity sensor hole 508, location sensor hole 510, and LED hole 512.

PCB 520 is constructed similarly to PCB 300 of FIG. 3A, such that processor 522 having memory 524 and communication chip 526, proximity sensor 528, location sensor 530, and LED 532 (optional) corresponds to processor 302 having memory 304 and communication chip 306, proximity sensor 308, location sensor 310, and LED 312 (optional) of PCB 300. In addition, processor 522 may be operatively coupled to a target reader corresponding to target reader 314, a user ID reader corresponding to user ID reader 316, and a cartridge verifier corresponding to cartridge verifier 318. In FIG. 5A, components of processor 522 are not depicted to scale on either a relative or absolute basis. PCB 520 differs from PCB 300 in that PCB 520 may have power source 534 directly affixed to PCB 520, wherein power source 534 delivers power to the components of PCB 520 and to motor 509 described in more detail below. PCB 520 may be affixed to the backside of flat back portion 514 of frame 500 such that proximity sensor 528, location sensor 530, and LED 532 aligns with proximity sensor hole 508, location sensor hole 510, and LED hole 512, respectively, of flat back portion 514.

Figure 5B:
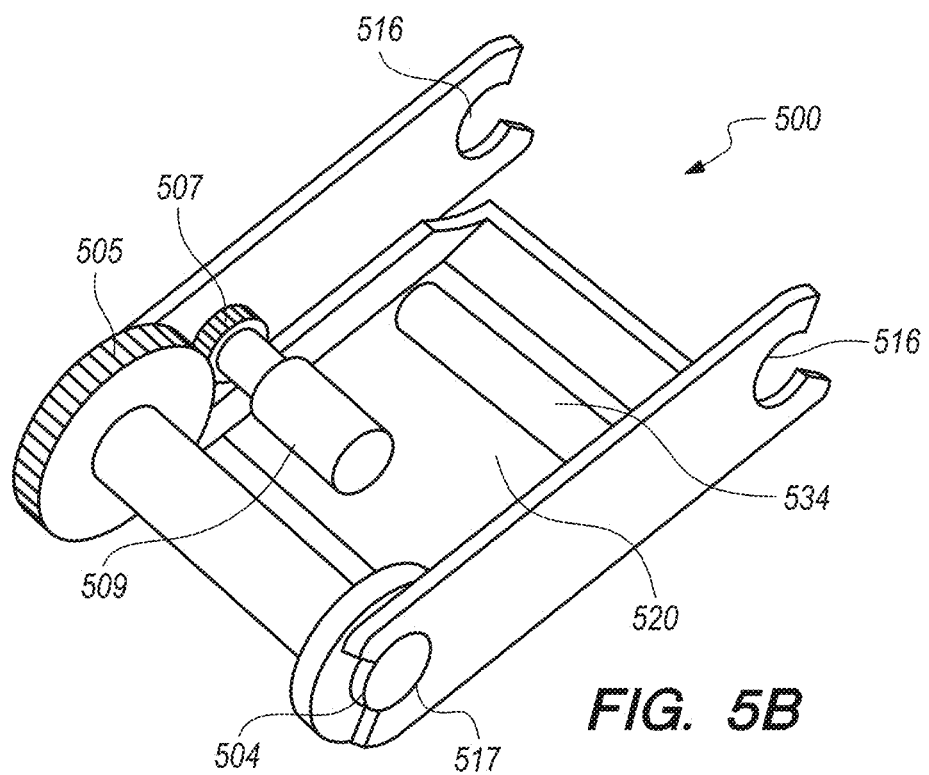
Figure 5C:
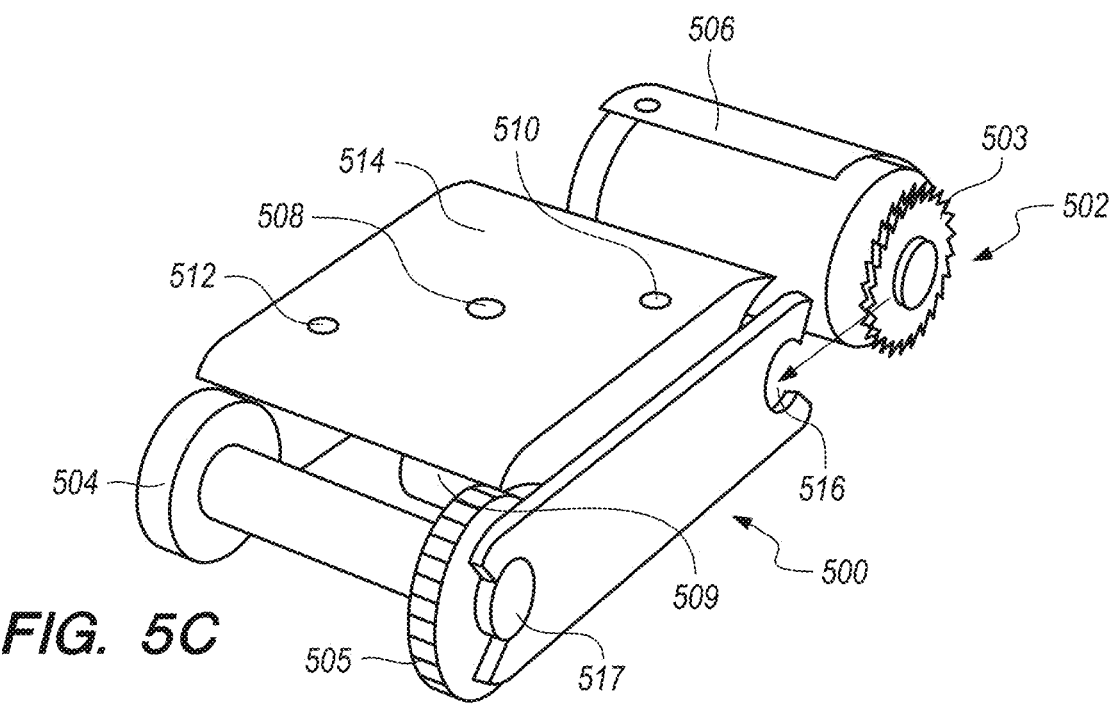

FIG. 5B illustrates the backside of spool frame 500 wherein second spool 504 is coupled to frame 500 by engaging the opposite ends of second spool 504 within second spool notches 517. As shown in FIG. 5B, motor 509 and frame gear 507 may be affixed to spool frame 500 such that frame gear 507 engages with spool gear 505 of second spool 504 when second spool 504 is coupled to frame 500. As shown in FIG. 5C, first spool 502 may be coupled to frame 500 by engaging the opposite ends of first spool 502 within first spool notches 516. As one skilled in the art would understand, the ends of first spool 502 may have a diameter larger than the diameter of the center axis of first spool 502 such that a roll of backing member 506 may be contained in between the ends of first spool 502.

Figure 5D:
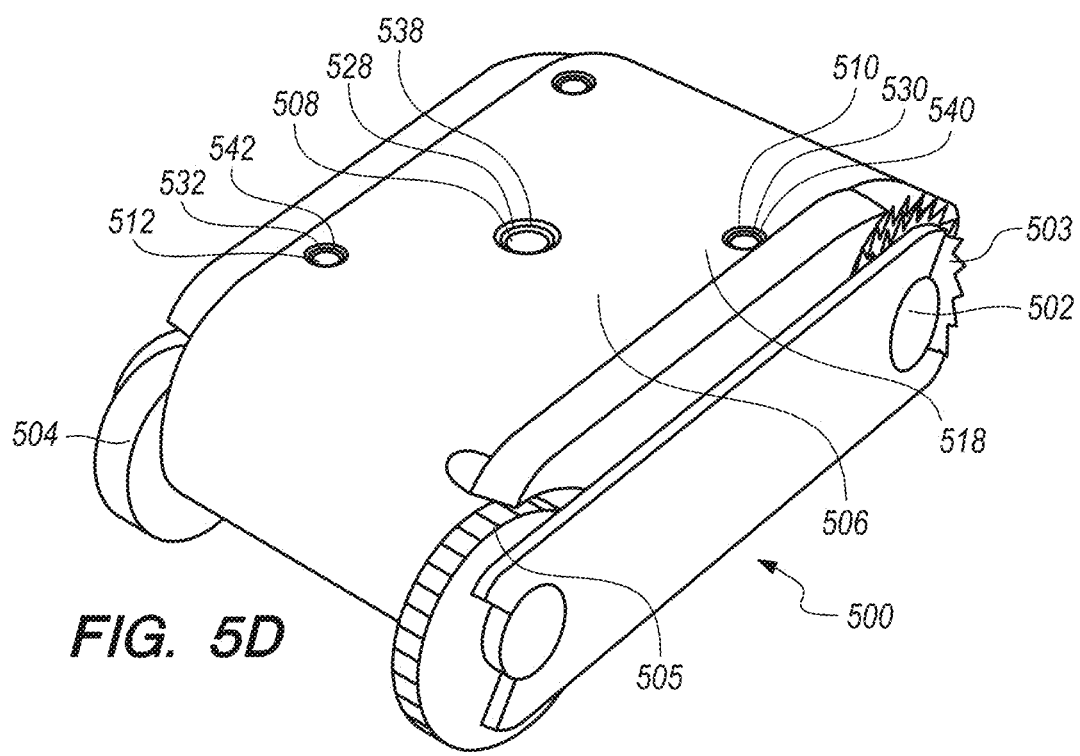

As shown in FIG. 5D, a portion of backing member 502 may be pulled from the roll of backing member 506 disposed on first spool 502 and wrapped around and affixed to the center axis of second spool 504. A portion of backing member 506 disposed between first spool 502 and second spool 504 forms flat area 518, which rests against flat portion 514 of frame 500. As one skilled in the art would understand, the ends of second spool 504 may have a diameter larger than the diameter of the center axis of second spool 504 such that a roll of backing member 506 may be contained in between the ends of second spool 504.

Figure 6A:
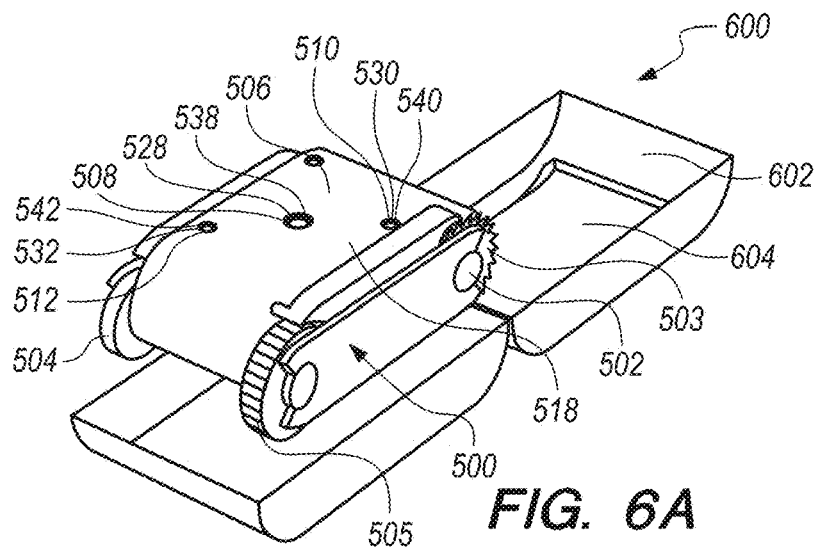
FIGS. 6A through 6C show another exemplary cartridge of a kit for dispensing disposable stethoscope covers wherein the spool frame of FIGS. 5A through 5D is disposed within an exemplary cartridge housing constructed in accordance with the principles of the present disclosure.
Figure 6B:
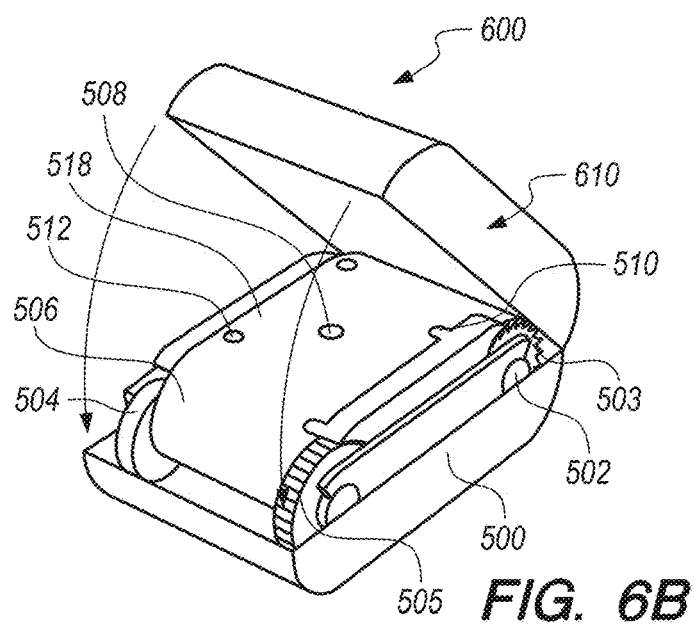
Figure 6C:
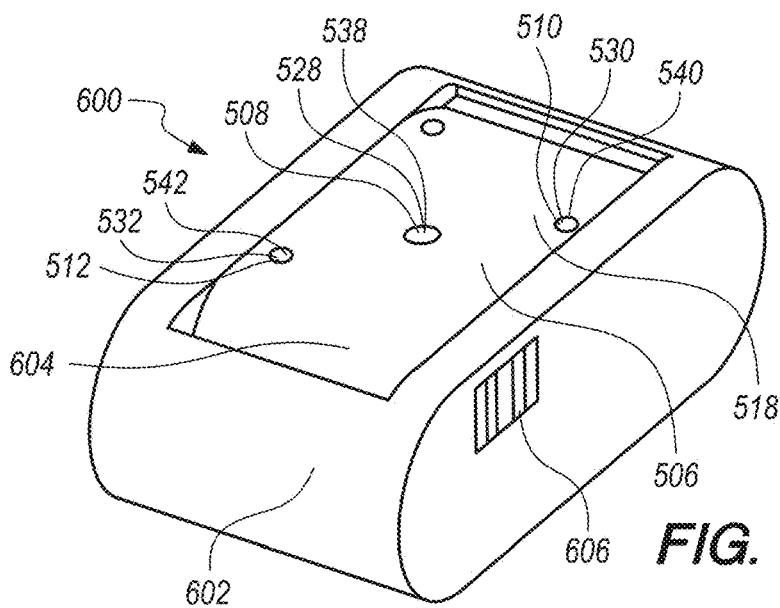

Referring now to FIGS. 6A through 6C, another exemplary cartridge of a kit for dispensing disposable stethoscope covers constructed in accordance with the principles of the present disclosure is described. Cartridge 600 comprises cartridge housing 602 which is sized and shaped to receive spool frame 500. Cartridge housing 602 is similar in size and shape to cartridge housing 110 of cartridge 100 of FIG. 1A. Spool frame 500, first spool 502, second spool 504, backing member 506, and the disposable stethoscope covers are sized and shaped to be self-contained within cartridge housing 602 such that backing member 506 transfers from first spool 502 to second spool 504, entirely within cartridge housing 602. As shown in FIG. 6A, cartridge housing 602 comprises cartridge window 604. Cartridge window 604 is sized to permit exposure of backing member 506 and the disposable stethoscope covers disposed thereon from within cartridge housing 602 such that the disposable stethoscope covers may be attached to a stethoscope head.

As shown in FIG. 6B, cartridge housing 602 may transition from an open configuration to a closed configuration wherein spool frame 500, first spool 502, second spool 504, backing member 506, and the disposable stethoscope covers are self-contained within cartridge housing 602.

FIG. 6C illustrates cartridge 600 wherein cartridge housing 602 is in the closed configuration such that spool frame 500, first spool 502, second spool 504, backing member 506, and the disposable stethoscope covers are self-contained within cartridge housing 602. Similar to cartridge housing 110 of FIG. 2, cartridge housing 602 may include a protrusion that engages with sprocket 503 to permit first spool 502 to rotate unidirectionally toward second spool 504, e.g., counter-clockwise, and prevent the roll of backing member 506 from unraveling within cartridge housing 602. As shown in FIG. 6C, flat area 518 of backing member 106 is exposed through cartridge window 604. The portion of backing membrane 506 forming flat area 518 in FIG. 6C is shown without a disposable stethoscope cover in a ready-to-dispense position. In one embodiment, backing member 506 may comprise proximity sensor hole 538, marker 540, and LED hole 542, in proximity to the location of each disposable stethoscope cover disposed on backing member 506. As shown in FIG. 6C, proximity sensor 528, location sensor 530, and LED 532 of PCB 520 are aligned with proximity sensor hole 508, location sensor hole 510, and LED hole 512, respectively, of flat portion 514 of spool frame 500, and with proximity sensor hole 538, marker 540, and LED hole 542, respectively, of backing member 506. As shown in FIG. 6C, cartridge housing 602 may further include specified marker 606, e.g., physical marker, electrical marker, or barcode, such that a dispenser designed to receive cartridge 600 will only be compatible with cartridges having the specified marker as described in further detail below.

Figure 7A:
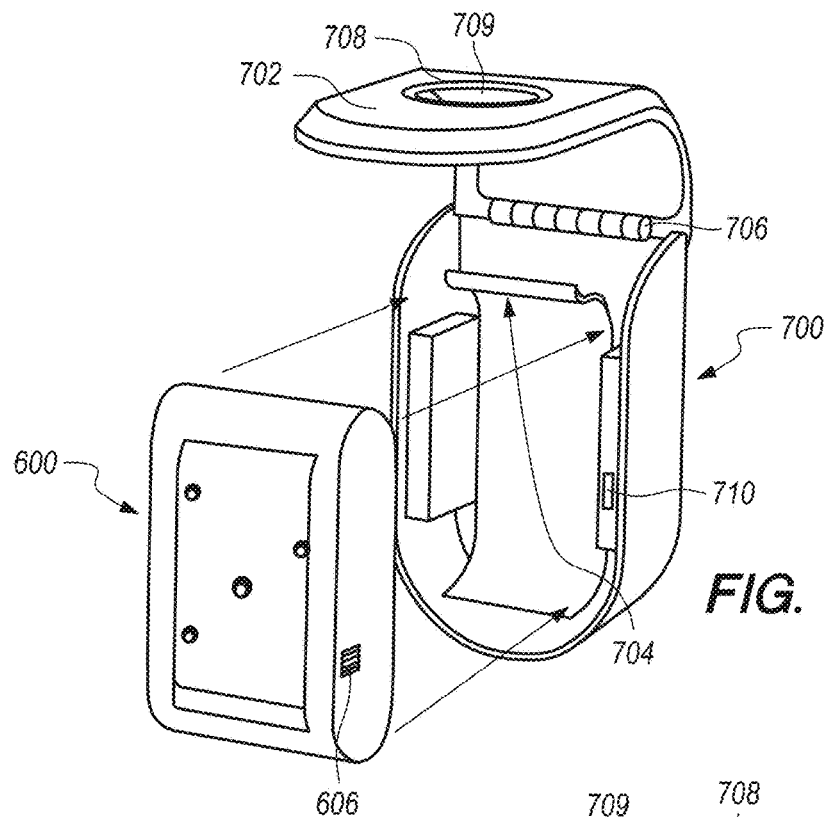
FIG. 7A illustrates the insertion of the cartridge of FIGS. 6A through 6C into another exemplary dispenser for dispensing disposable stethoscope covers constructed in accordance with the principles of the present disclosure.
Figure 7B:
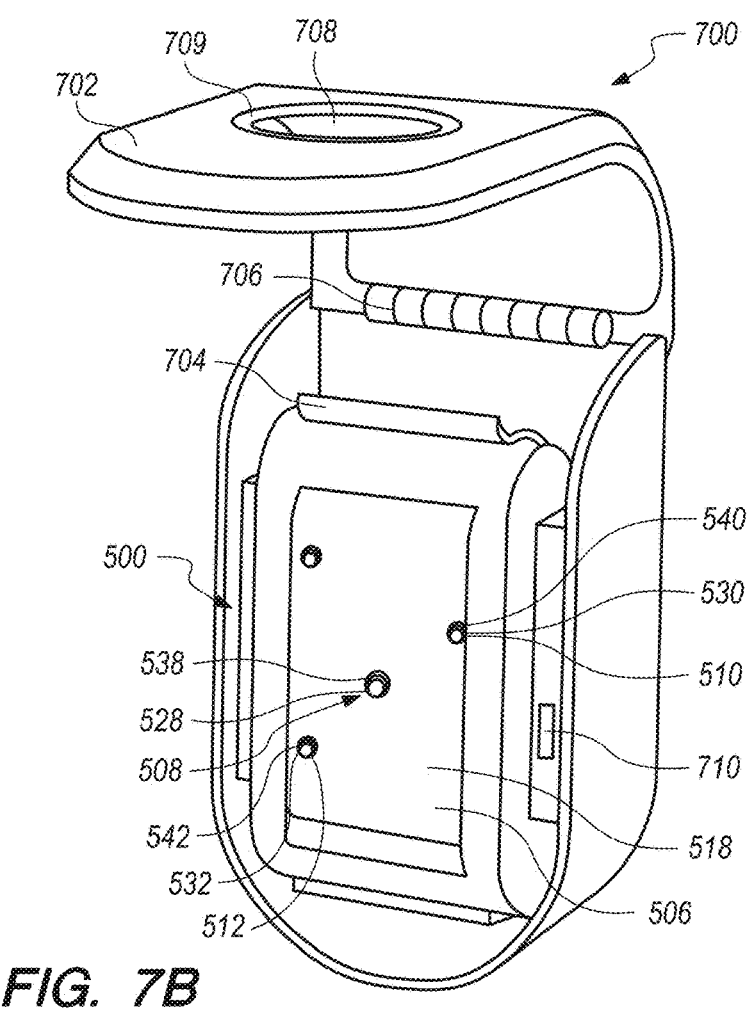
FIG. 7B shows the cartridge of FIGS. 6A through 6C inserted within the dispenser of FIG. 7A in an open configuration.

Referring now to FIGS. 7A through 7D, the insertion of cartridge 600 into another exemplary dispenser for dispensing disposable stethoscope covers constructed in accordance with the principles of the present disclosure is described. As shown in FIG. 7A, dispenser 700 comprises cartridge clamp 704 for removably securing cartridge 600 within dispenser 700, and front panel 702 having dispenser window 708 and location ring 709, wherein front panel 702 may pivot about dispenser hinge 706 such that dispenser 700 may transition between an open configuration and a closed configuration. Dispenser 700 is designed to be easily cleaned, e.g., rounded edges, and may be wall-mounted to hold cartridge 600 in a readily accessible orientation and position. As described above, dispenser 700 may include cartridge verifier 710 such that dispenser 700 will only be compatible with cartridges having specified marker 606, e.g., physical marker, electrical marker, or barcode. FIG. 7B shows dispenser 700 with cartridge 600 positioned within dispenser 700, removably secured via clamp 704.

Dispenser 700 having cartridge 600 disposed therein functions in a similar manner to dispenser 400 having cartridge 100 disposed therein. For example, as described above, upon detection of a user by proximity sensor 528, processor 522 may cause motor 509 to rotate gear 507 which causes the rotation of spool gear 505 and accordingly second spool 504. The rotation of second spool 504 causes backing member 506 to travel from first spool 502 to second spool 504. Therefore, as a disposable stethoscope cover is removed from backing member 506, the spent backing member is collected by second spool 504 and self-contained within cartridge housing 602.

Figure 7C:
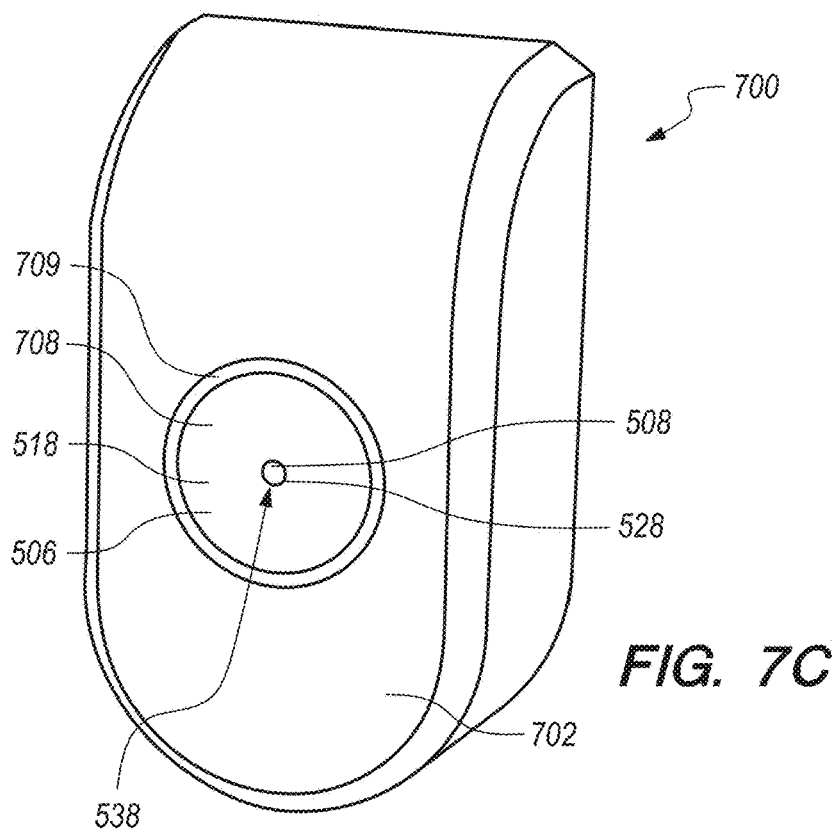
FIG. 7C shows the dispenser of FIG. 7B in a closed configuration.

FIG. 7C illustrates dispenser 700 in a closed configuration with cartridge 600 disposed therein. As shown in FIG. 7B, flat area 518 of backing member 506 is aligned with and exposed through dispenser window 708. Additionally, proximity sensor 528 is aligned with proximity sensor hole 508 of flat area portion 514 and proximity sensor hole 538 of backing member 506. Location ring 709 may encircle dispenser opening 708 and may be adjacent to LED 532 when dispenser 700 is in a closed configuration. Location ring 709 may be composed of a translucent material such that location ring 709 illuminates when LED 532 lights up. In one embodiment, LED 532, aligned with LED hole 542, may illuminate a light, e.g., white, green, or blue, constantly while proximity sensor 528 is activated, causing location ring 709 to illuminate in a similar manner. This may be helpful in parts of the hospital that may be dark, such as an operating room, so the health care worker may locate dispenser window 708 and know where to place the stethoscope head to attach to a disposable stethoscope cover. As described above, the color of the light illuminated by LED 532, and accordingly location ring 709, may change depending on the quantity of disposable stethoscope covers remaining in cartridge 600.

Figure 7D:
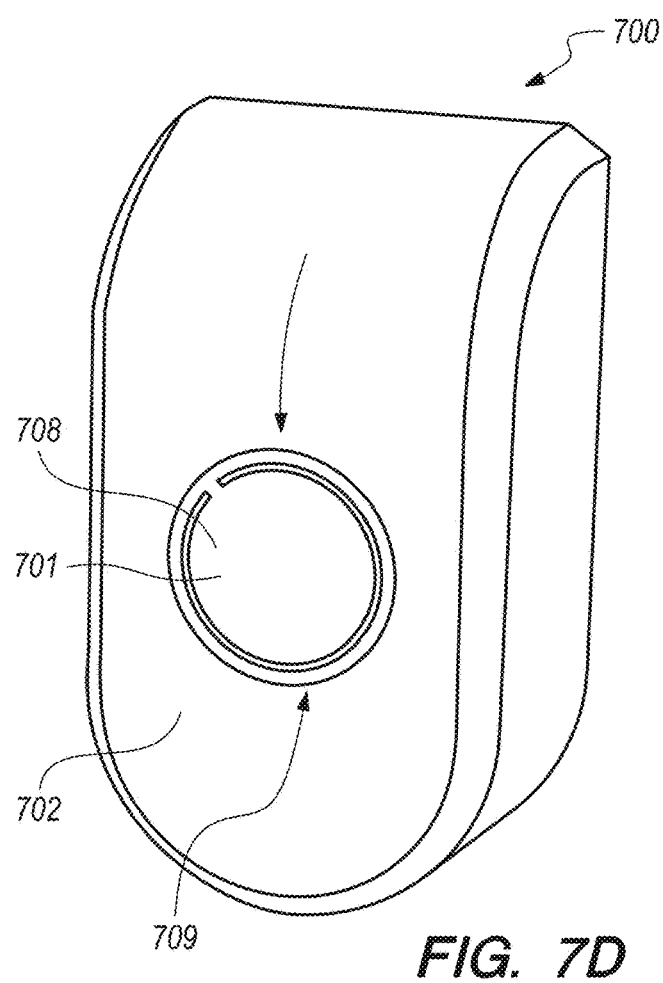
FIG. 7D shows the dispenser of FIG. 7C with a disposable stethoscope cover aligned with the dispenser window.

FIG. 7D illustrates dispenser 700 having disposable stethoscope cover 701 aligned with dispenser window 708, ready for a user, e.g., health care worker, to position a stethoscope head within dispenser window 708 to contact and adhere to disposable stethoscope cover 701, and to remove disposable stethoscope cover 701 from flat area 518 of backing member 506. As described above, after the target reader or proximity sensor 528 detects that disposable stethoscope cover 701 has been removed from backing member 506, processor 522 may delay reactivation of proximity sensor 528. After a predetermined amount of time, proximity sensor 528 may be reactivated such that proximity sensor 528 is able detect a user, permitting a subsequent disposable stethoscope cover to be moved to the ready-to-dispense position. As described above, location ring 709 may communicate to a user the quantity of disposable stethoscope covers remaining in cartridge 600. Accordingly, when cartridge 600 is ready to be replaced, front panel 702 of dispenser 700 may be moved to an open configuration so that empty cartridge 600 may be removed from dispenser 700 by disengaging empty cartridge 600 clamp 704 within dispenser 700, and a full cartridge may be inserted into dispenser 700.

Figure 8:
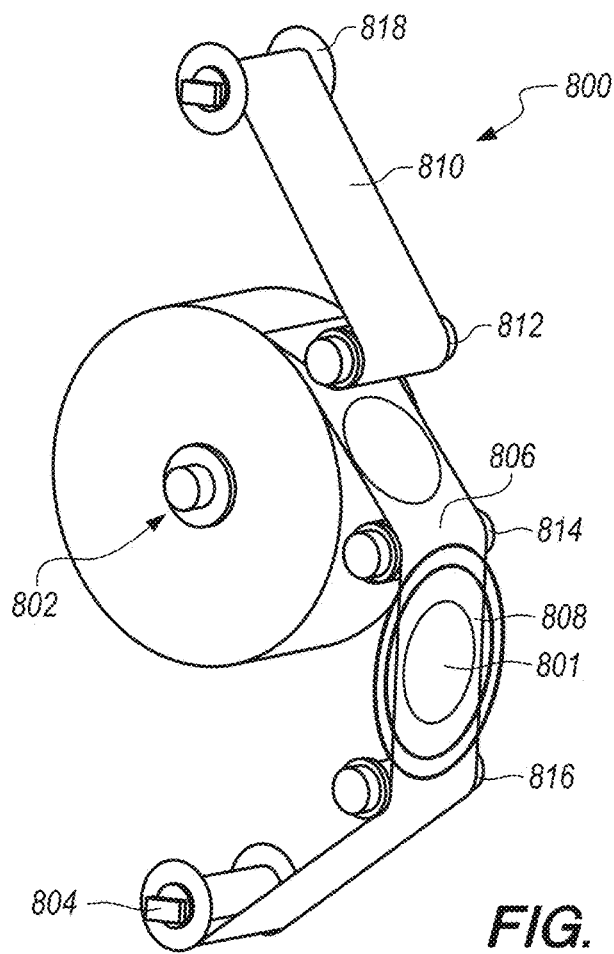
FIG. 8 shows another exemplary spool system constructed in accordance with the principles of the present disclosure.

Referring to FIG. 8, another exemplary spool system constructed in accordance with the principles of the present disclosure is described. Spool system 800 comprises disposable stethoscope covers 801, supply spool 802, collection spool 804, backing member 806, protective tape 810, first idler 812, second idler 814, third idler 816, and tape spool 818. Disposable stethoscope cover 801, supply spool 802, collection spool 804, and backing member 806 may be constructed similarly to disposable stethoscope cover 101, 701, first spool 102, 502, second spool 104, 504, and backing member 106, 506, respectively, as described above. Backing member 806 travels from supply spool 802 toward collection spool 804. Before reaching collection spool 804, backing member travels over second idler 814 and third idler 816 to form flat area 808 between second idler 814 and third idler 816. Flat area 808 functions similarly to flat area 108 and flat area 518 described above, to provide a taut area of backing member 806 for a stethoscope head to attach to disposable stethoscope cover 801. Alternatively, spool system 800 may include a spool frame having a flat back portion similar to spool frame 500 having flat back portion 514, instead of second idler 814 and third idler 816 to form flat area 808. In yet another alternative embodiment, spool system 800 may not include second idler 814 and third idler 816, and flat area 808 may be formed as described in FIGS. 1A-1D wherein a backing element of a dispenser forms flat area 808 of backing member 806.

Backing member 806 having disposable stethoscope covers 801 disposed thereon may include protective tape 810 such that disposable stethoscope covers 801 are sandwiched between backing member 806 and protective tape 810. Protective tape 810 may be made of a thin and flexible material known in the art to protect disposable stethoscope covers 801 without causing disposable stethoscope covers to adhere to protective tape 810 when protective tape 810 is removed from backing member 806. As shown in FIG. 8, protective tape 810 is removed from backing member 806 before backing member 806 forms flat area 808 between second idler 814 and third idler 816. As protective tape 810 is removed from backing member 806, protective tape 810 moves about first idler 812 toward tape spool 818 such that tape spool 818 collects protective tape 810 as backing member moves from supply spool 802 to collection spool 804. Tape spool 818 may be designed to rotate analogously with collection spool 804 such that the amount of protective tape 810 that is collected by tape spool 818 is equal to the amount of spent backing member 806 collected by collection spool 804.

Spool system 800 may be sized and shaped to be self-contained within cartridge housing 110 and/or cartridge housing 602. Supply spool 802 may comprise a sprocket that prevents unraveling of backing member 806 rolled about supply spool 802 as described above. Additionally, collection spool 804 may comprise a collection spool gear that engages with a gear coupled to a motor for rotating collection spool 804 as described above.

Figure 9:
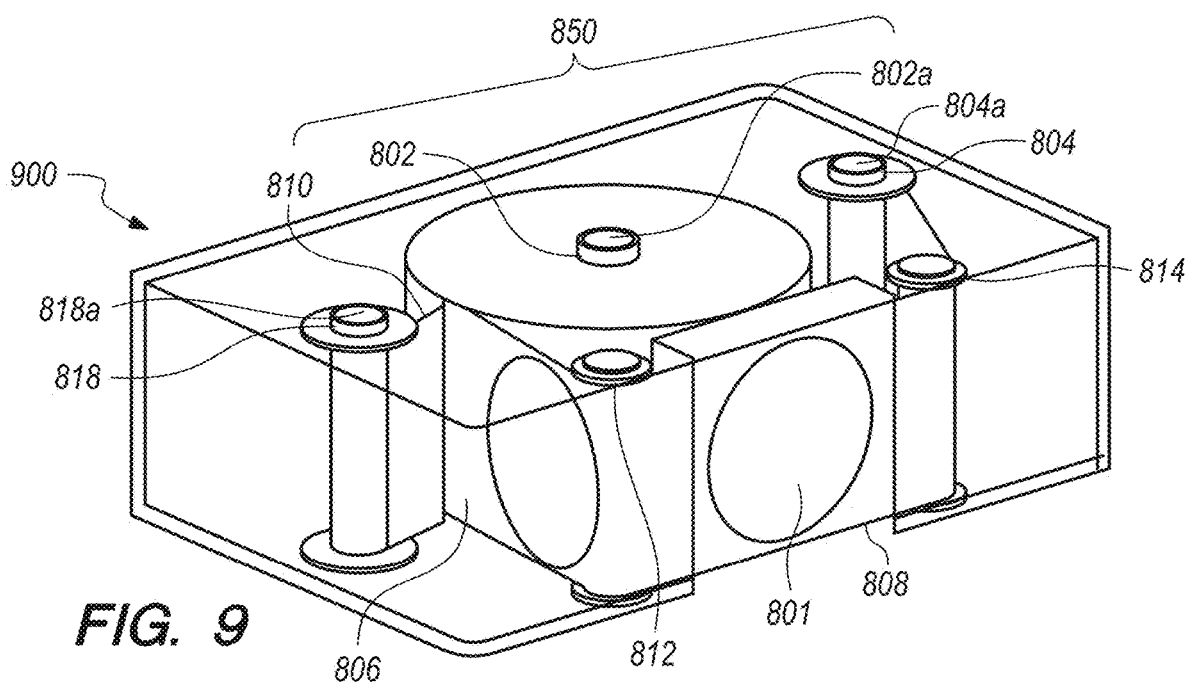
FIG. 9 shows another embodiment of the spool system of the present invention embedded in an exemplary cassette system of the present disclosure.

As shown in FIG. 9, an alternative embodiment to the spool system of the present disclosure is provided, as displayed within a cassette system embodiment of the present invention. Cassette 900 houses a spool system 850 similar to spool system 800 described in FIG. 8. In this embodiment, disposable stethoscope cover 801, as applied on backing member 806, first travels from supply spool 802 through tape spool 818 to remove protective tape 810. In this embodiment, tape spool 818 may comprise a spool gear that engages with a gear coupled to a motor positioned below the cassette 900 for rotating the tape spool 818 as described herein. As protective tape 810 is removed from backing member 806, protective tape 810 is spooled around the tape spool 818 from the motor driven operation such that tape spool 818 collects protective tape 810 as backing member 806 moves from supply spool 802 to, eventually, collection spool 804.

As protective tape 810 is removed from backing member 806 by tape spool 818, backing member 806 travels over first idler 812 and second idler 814 to form flat area 808 between first idler 812 and second idler 814. Disposable stethoscope cover 801 is displayed in a central location across the area formed by flat area 808 to provide a taut resistance within backing member 806 across flat area 808 to accommodate a stethoscope head to attach to disposable stethoscope cover 801.

As each disposable stethoscope cover 801 is removed, the backing member 806 continues over second idler 814 towards collection spool 804, where collection spool 804 collects spent backing member 806 each time a disposable stethoscope cover 801 is removed from flat area 808. Tape spool 818 may be designed to rotate in accordance with collection spool 804 such that the amount of protective tape 810 that is collected by tape spool 818 is roughly equal to the amount of spent backing member 806 collected by collection spool 804.

Each spool has a hollow port associated with the spool, wherein the hollow port of each spool runs from the top of the cassette to the bottom of the cassette. Tape spool 818 comprises tape spool port 818a, supply spool 802 comprises supply spool port 802a and collection spool 804 comprises collection spool port 804a.

Spool system 850 may be sized appropriately, depending on desired size of cassette 900 and other relevant parameters. Optionally, spool system 850 may further comprise a third idler positioned in a location to allow for greater tautness of backing member 806.

Figure 10:
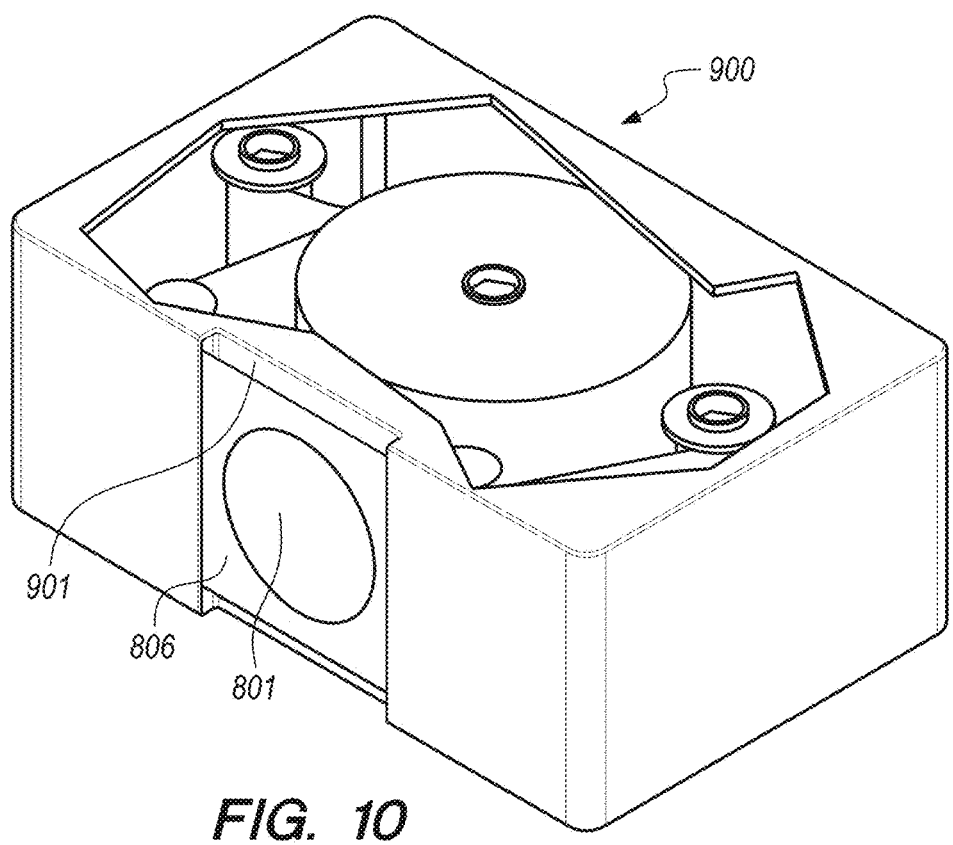
FIG. 10 shows a preferred embodiment of the cassette housing the preferred spool system of the present disclosure.

FIG. 10 shows a preferred embodiment of cassette 900, with a cutaway view of the preferred spool system 850 described herein. The front face of cassette 900 comprises a recessed area centrally positioned that defines the resistance section 901 of cassette 900. Resistance section 901 may be utilized to provide appropriate resistance to backing member 806 for a stethoscope head to attach to disposable stethoscope cover 801 such that as a stethoscope head is pressed into the disposable stethoscope cover 801, there is sufficient resistance behind backing member 806 to firmly attach the disposable stethoscope cover 801 to stethoscope head and allow for a sufficiently strong attachment to then allow for the disposable stethoscope cover 801 to be removed from the backing member 806.

Figure 11:
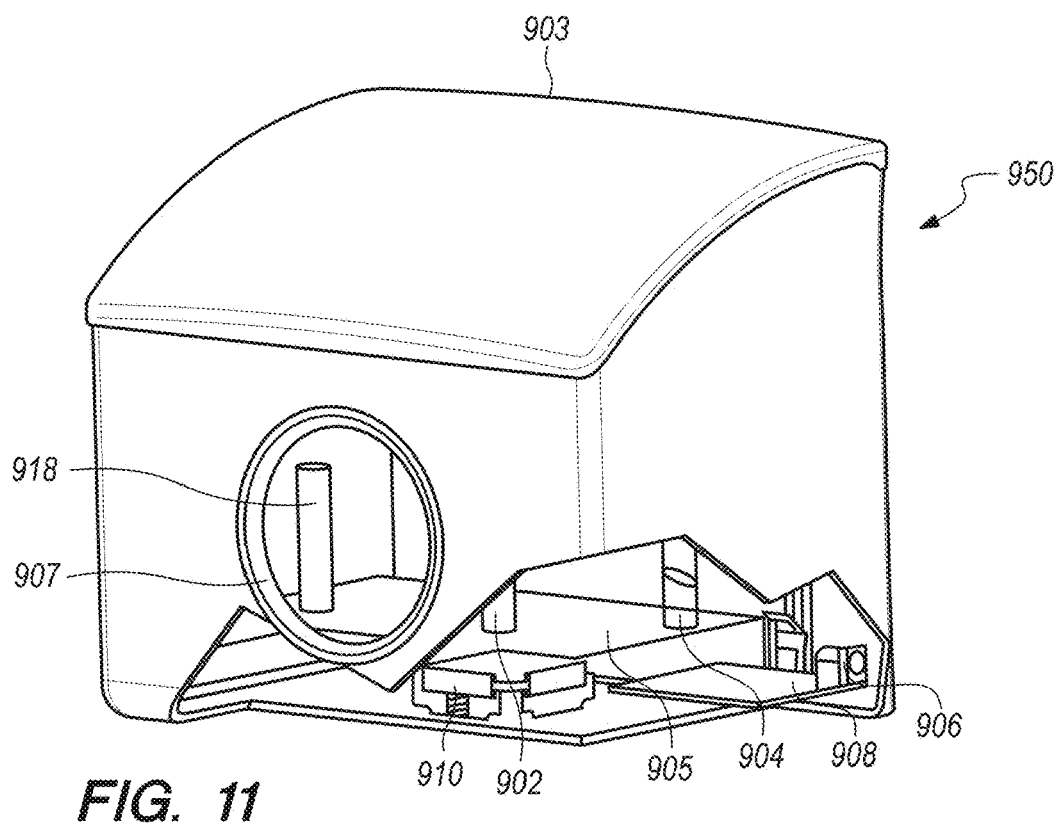
FIG. 11 shows the housing assembly of the present disclosure and cutaway sections detailing the interior of the assembly housing.

According to FIG. 11, the present invention further describes a housing assembly 950 which houses cassette 900. Housing assembly 950 may comprise arced lid 903 to cover the cassette 900 once inserted into housing assembly 950. Preferably, the arced lid 903 is curved such that there is no flat surface on arced lid 903, whereby anything placed on top of arced lid 903 will likely slide down and off housing assembly 950. Cassette 900 is placed inside of housing assembly 950 by alignment of each of the three spools with the corresponding drive shafts: tape spool 818 is paired with tape spool drive shaft 918 via tape spool port 818a, supply spool 802 is paired with supply spool drive shaft 902 via supply spool port 802a and collection spool 804 is paired with collection spool drive shaft 904 via collection spool port 804a. Once cassette 900 is aligned according to the above-described pairings, it is lowered into housing assembly 950 until cassette flooring 905 is reached. Each of the drive shafts may be attached to cassette flooring 905. Optionally, each of the drive shafts may extend beyond cassette flooring 905 and attach at a lower point within housing assembly 950. Preferably, at least one drive shaft is connected to a motor 910 that provides power to at least one gear responsible for driving the motion of tape spool 818.

Motor 910 may be mounted under and directly attached to the drive shaft responsible for driving the motion of at least one spool. Alternatively, motor 910 may be mounted under another drive shaft, where such drive shaft is not the one responsible for driving the motion of the active spool. Optionally, motor 910 may operate more than one drive shaft and may mounted under a drive shaft that is not operational. Motor 910 may be AC/DC, hardwired into an external power source, battery operated or a combination thereof.

Positioned below cassette flooring 905 is at least one USB port 906 connected to port shelf 908. Optionally, other indicators may be mounted on or to port shelf 908 including power indicators, status buttons, etc. Port shelf 908 may be positioned on the side, rear or front of housing assembly 950.

Access window 907 is centrally positioned on the front face of housing assembly 950. Preferably, each disposable stethoscope cover 801 is centered within access window 907 as backing member 806 cycles through spool system 850. Access window 907 may comprise a bezel, with or without lights. Preferably, the lighted bezel is in the form of a LED bezel, but any light source with can accommodate the bezel dimension of access window 907 would be considered part of the present disclosure.

Figure 12A:
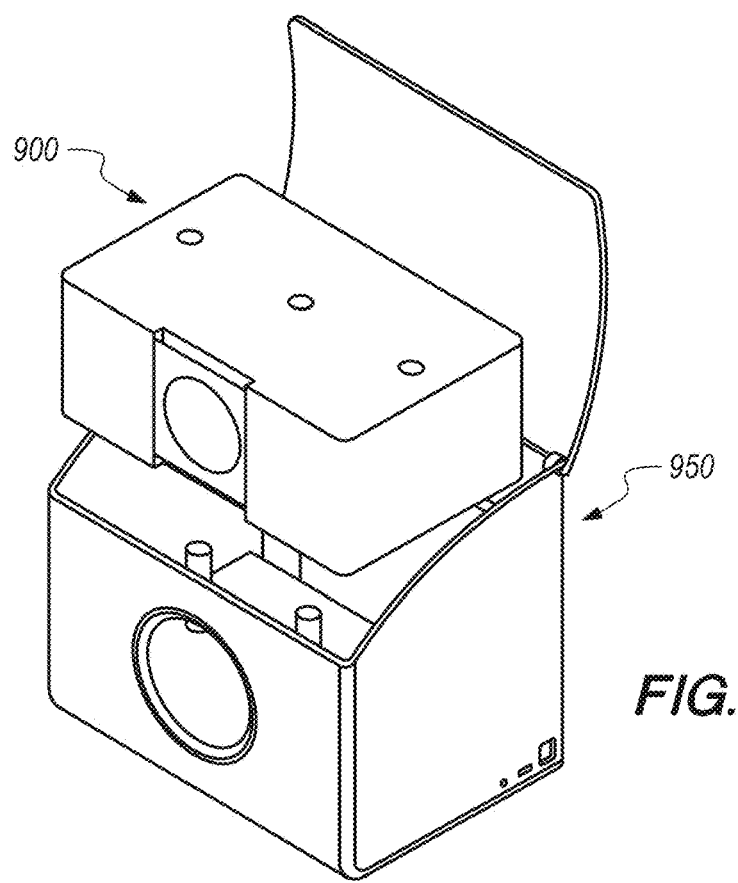
FIG. 12A shows preliminary alignment of cassette as it enters the housing assembly.
Figure 12B:
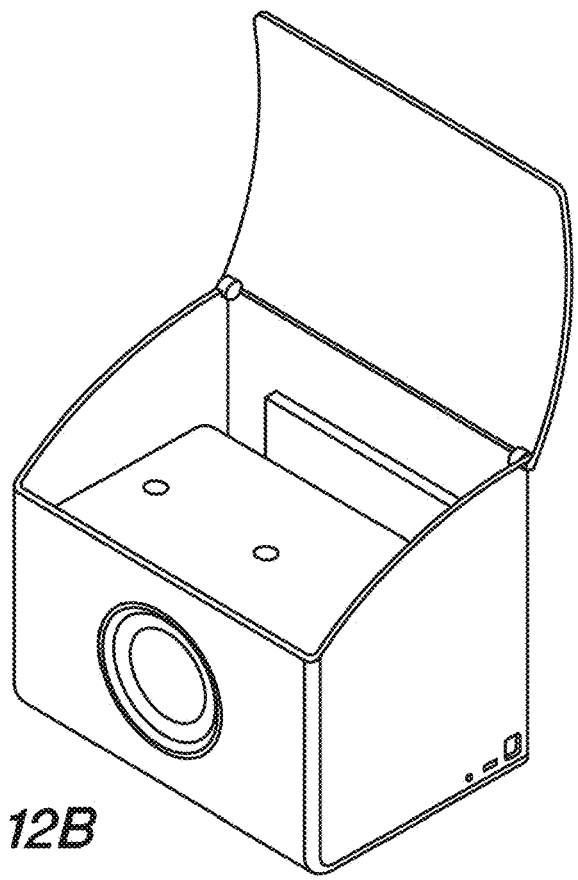
FIG. 12B shows the cassette fully installed within the housing assembly.

FIG. 12A shows a representation of the installation of cassette 900 into housing assembly 950. As shown, cassette 900 is positioned such that each spool port is paired with the respective drive shaft from within housing assembly 950. FIG. 12B shows a fully installed cassette 900 into housing assembly 950.

Figure 13:
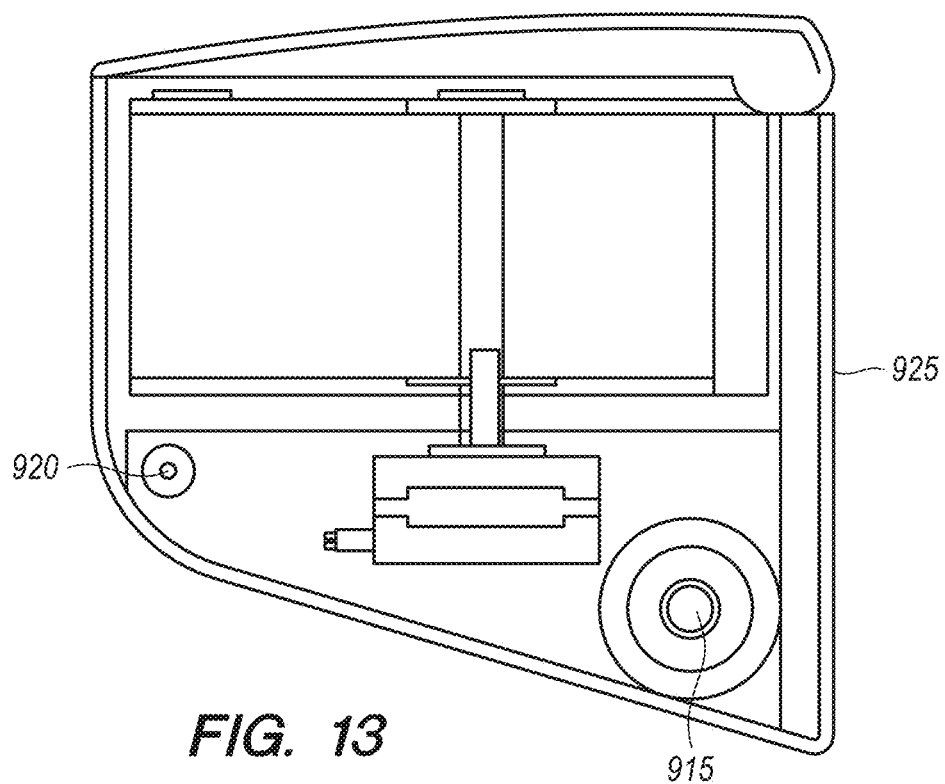
FIG. 13 shows a transparent side view of the preferred embodiment of the housing assembly with cassette installed.

FIG. 13 shows a side view of housing assembly 950 with cassette 900 installed. The view is transparent to provide clarity to the internal arrangement of the componentry. Battery 915 shows a preferred position within housing assembly 950. Battery 915 may comprise multiple batteries, a battery pack or a single battery to operate motor 910. Battery 915 may comprise disposable batteries, rechargeable batteries, or a combination thereof. Gate 920 is the power port to motor 910, thereby allowing the housing assembly 950 to be operated by AC power, DC power (or both), as well as providing a charge to battery 915 for recharging purposes. Rear mounting surface 925 is appropriately suited for mounting to a wall or some similar location.

Figure 14A:
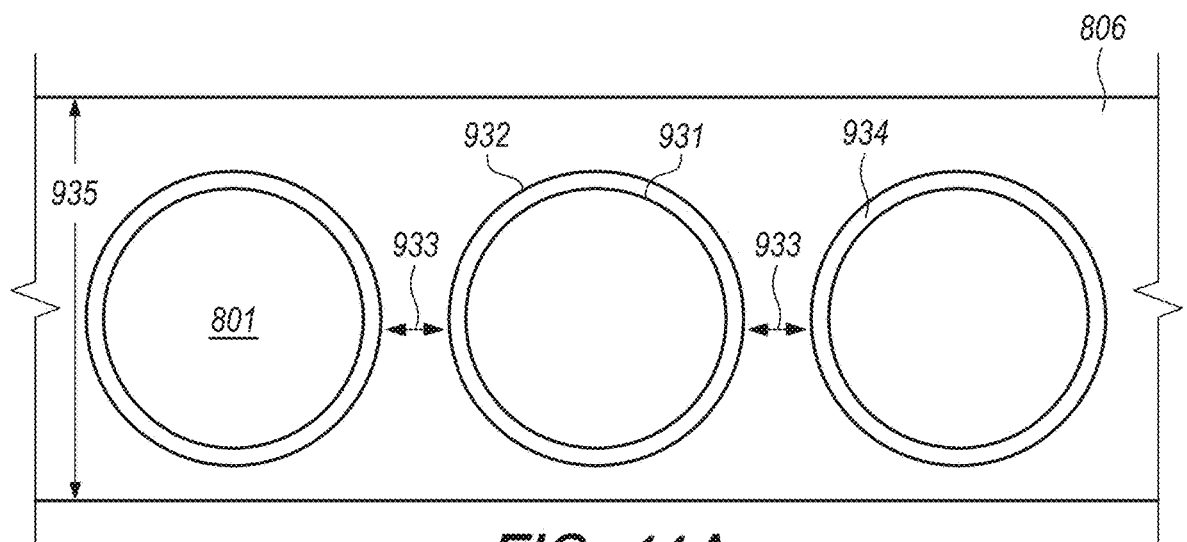
FIG. 14A shows a preferred arrangement of disposable stethoscope covers disposed on the backing member.
Figure 14B:
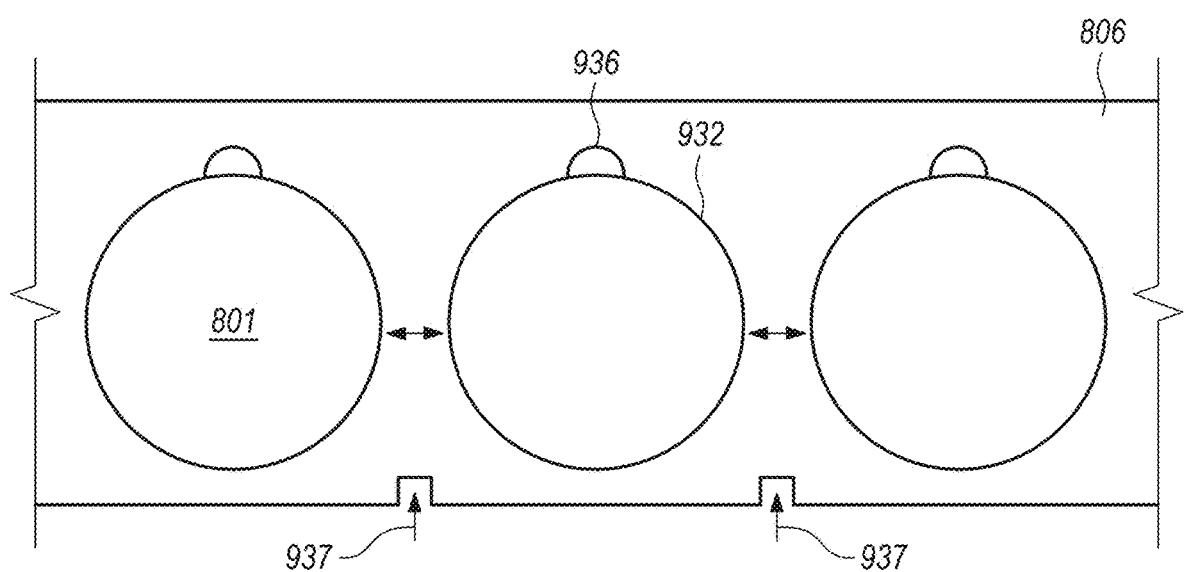
FIG. 14B shows an alternative embodiment of the backing member of the present disclosure.

Referring to FIGS. 14A and 14B, exemplary representations of a roll of backing member 806 providing a plurality of disposable stethoscope covers 801 are described. FIG. 14A illustrates one embodiment of a preferred arrangement of at least one disposable stethoscope cover 801 along backing member 806 from the viewpoint the exposed adhesive of each disposable stethoscope cover 801 as it is facing outward. Each disposable stethoscope cover 801 has an inner circumference 931 and an outer circumference 932, such that the difference between inner circumference 931 and outer circumference 932 ranges from about 0 to about 0.5 inches. Preferably, the inner circumference 931 more closely approximates the circumference of a stethoscope head, with the outer circumference 932 being about equal to or larger than the stethoscope head. Spacing 933 between each disposable stethoscope cover 801 ranges from about 0 inches to about 0.5 inches. Optionally, spacing 933 may be greater than 0.5 inches. Preferably, spacing 933 is between 0.15 to 0.35 inches. Optionally, dry ring 934 defines the area between the inner circumference 931 and outer circumference 932 and may be used to assist in peeling or removing disposable stethoscope cover 801 during application to stethoscope head. Width 935 of backing member 806 ranges from about 2 inches to about 4 inches, with a preferred range of about 2 inches to about 3 inches.

FIG. 14B illustrates an alternative, preferred embodiment of backing member 806 as described herein. Similar to FIG. 14A, exposed adhesive to each of disposable stethoscope cover 801 is shown. Outer circumference 932 may comprise a dry lift tab 936 located at a certain position around outer circumference 932. Preferably, dry lift tab 936 is non-adhesive and is sized to accommodate a user's fingers by pulling up or on dry lift tab 936 to remove disposable stethoscope cover 801 during the application process onto a stethoscope head. Optionally, backing member 806 may comprise one or more timing mark 937 along the lower or upper limits of backing member 806. Timing mark 937 may be used by spool system 850, cassette 900, motor 910 or housing assembly 950 to allow for exact position of disposable stethoscope cover 801 at a preferred, centered location within access window 907.

Figure 15:
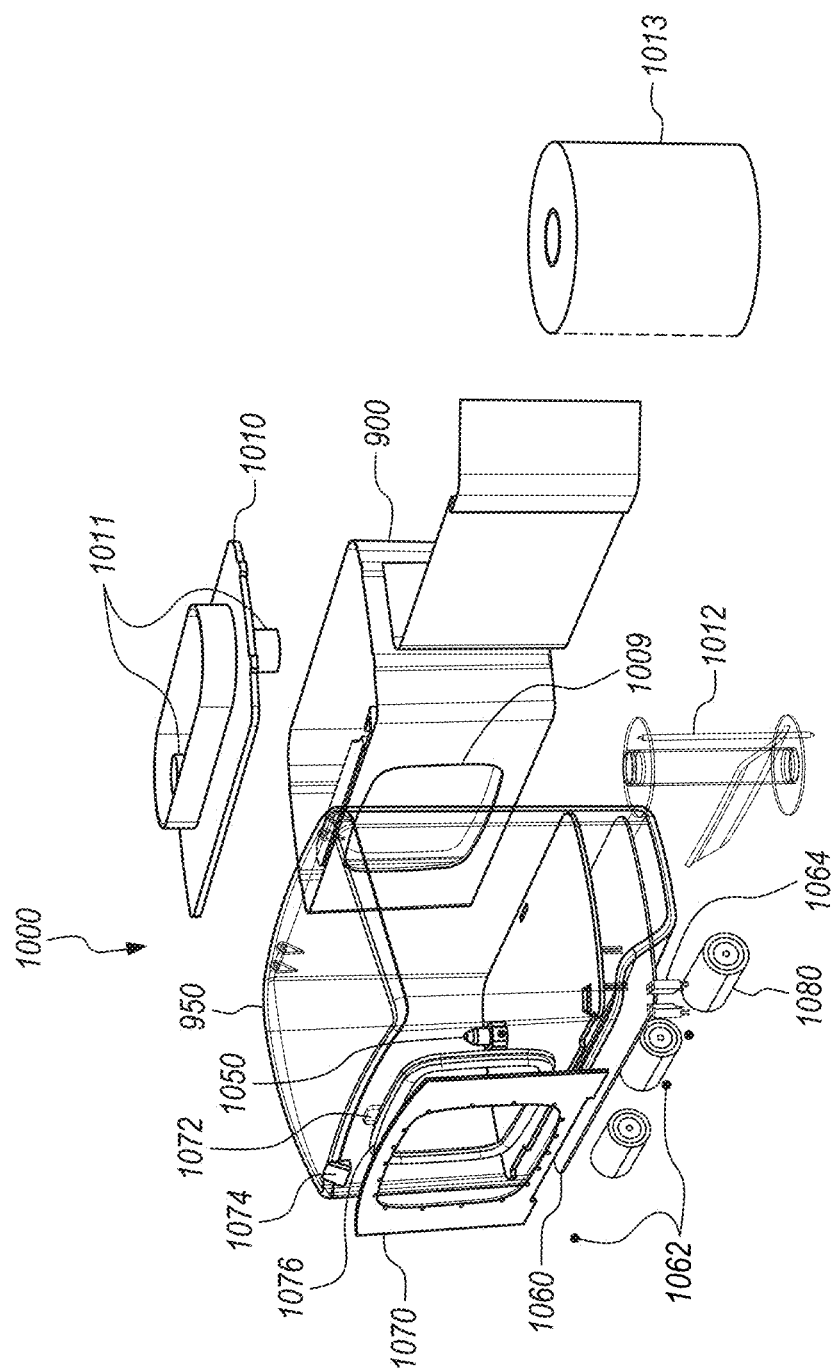
FIG. 15 shows an exploded view of the cassette and dispenser housing related to the disposable instrument cover embodiment of the present invention.

FIG. 15 illustrates an exploded view of another preferred embodiment of the present invention. In this aspect, it is desirable to accommodate other, more irregularly shaped instruments for use in application of a disposable cover to the irregularly shaped instrument, such as ultrasound probes. Probe kit 1000 is comprised of cassette 900 and housing assembly 950. Cassette lid 1010 is configured to fit over cassette 900 and comprises at least two separate spool structures 1011 to interface with the spools contained within the cassette.

In this embodiment, housing assembly 950 comprises a drive gear 1050 extending above the floor of housing assembly 950 while motor 910 sits directly underneath. Set immediately beneath the floor of housing assembly 950 is main printed circuit board assembly (PCBA) 1060 which further comprises indicator LEDs 1062 that indicates cassette status and battery levels. Main PCBA 1060 also includes a pair of location sensors 1064 used to identify the next probe cover in a center position relative to access window 907, which will then signal motor 910 to stop. In this embodiment, access window 907 is sized to accommodate an ultrasound probe for application of the probe cover to the probe, the size being largely square or rectangular in dimension. A cassette window 1009 is similarly sized in order to provide a visual alignment after cassette insertion into housing assembly 950.

Front PCBA 1070 is set behind the front face of housing assembly 950 and comprises a proximity sensor 1072 that indicates the presence of an ultrasound probe close enough to access window 907. Proximity sensor scoop 1074 is set just above access window 907 and light ring 1076 to more accurately determine distance of probe so probe cover can be readily accessed. Housing assembly 950 may be operated by AC power, DC power (or both), as well as providing a charge to batteries 1080 for recharging purposes.

Figure 16A:
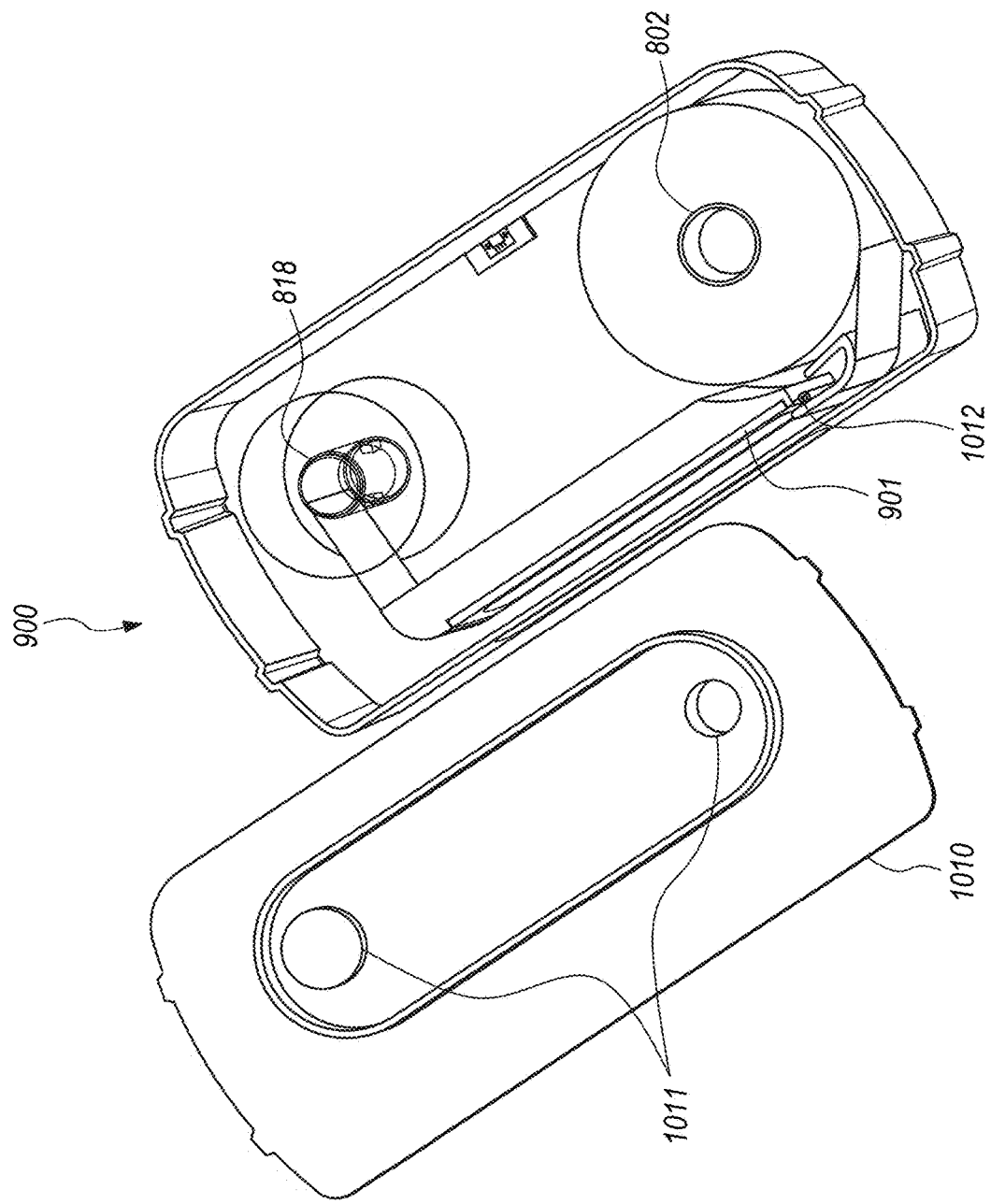
FIG. 16 shows a top view with lid removed (16A) and a perspective view from the underside as assembled (16B) of the cassette used in the disposable instrument cover embodiment of the present invention.
FIG. 16C shows how the partial separation of the disposable instrument cover/probe cover from the backing member occurs as the as the backing member migrates from supply spool to tape spool.

Cassette 900 is shown from a top view with lid 1010 removed in FIG. 16A. In this embodiment, cassette 900 comprises two spools: supply spool 802 and tape spool 818. Supply spool 802 is positioned to receive probe cover roll 1013 and tape spool 818 sits over drive gear 1050, which is connected to motor 910. Peeler pin 1012 is embedded within cassette 900 proximate to supply spool 802 to accommodate removal of probe covers from probe cover roll 1013. This serves to ease the transfer of the disposable instrument cover onto the instrument proper. Resistance section 901 is utilized to provide appropriate resistance to probe covers in order to detach probe cover once applied to probe and allow for a sufficiently strong attachment to then allow for the probe cover to be removed from probe cover roll 1013.

Figure 16C:
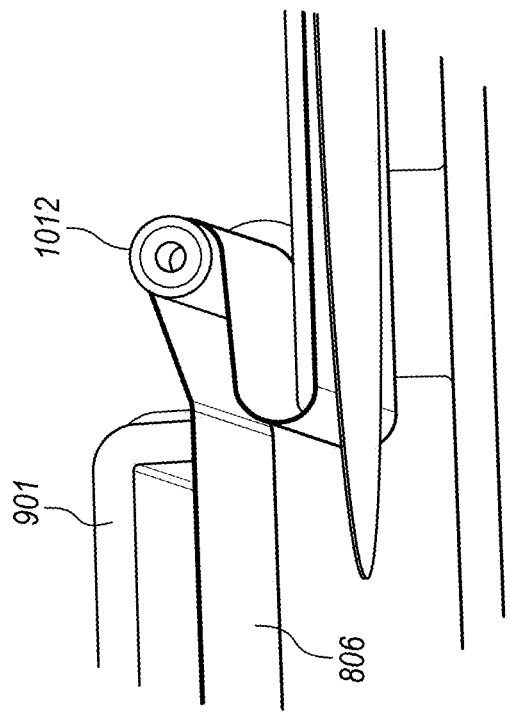
Figure 16B:
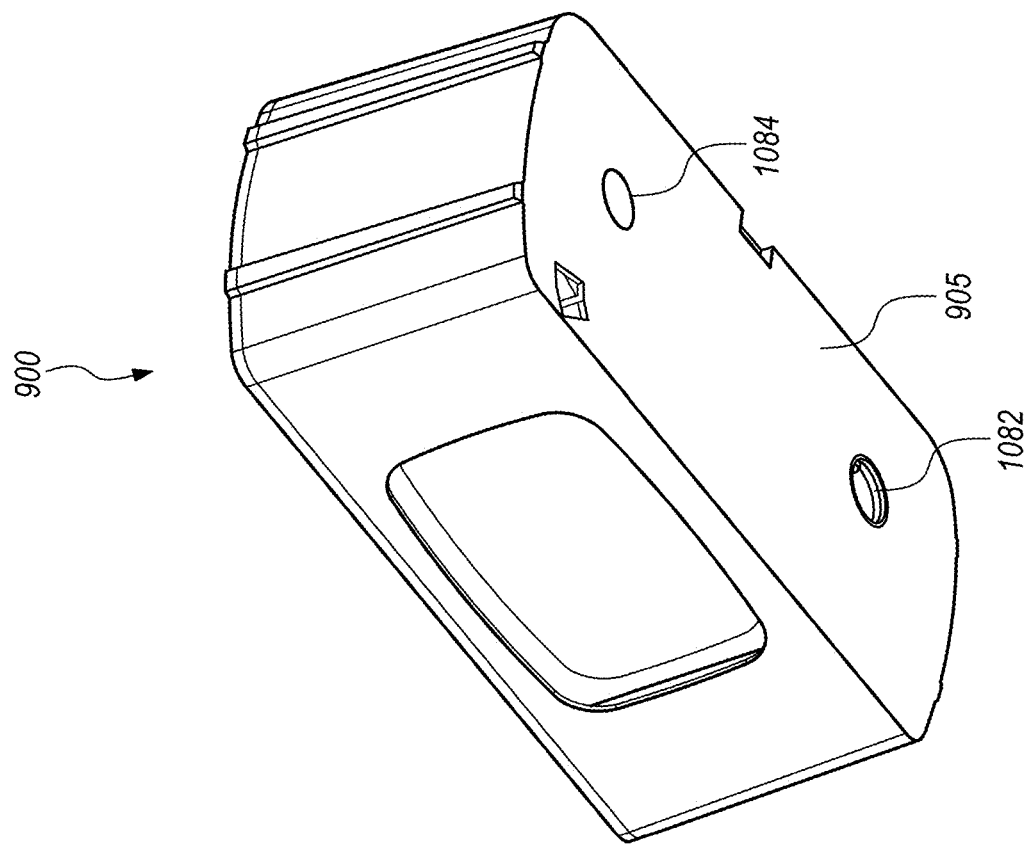

FIG. 16B shows a perspective view looking upwards from the underside of a fully assembled cassette 900. In this preferred embodiment, drive port 1082 and supply port 1084 can be observed located within cassette flooring 905. Drive port 1082 is sized to fit drive gear 1050 to rotationally operate tape spool 818 which, in turn, rotates supply spool 802, thereby causing probe cover roll 1013 to deliver probe covers to the center of cassette window 1009, at which time motor 910 will stop to allow probe covers to be dispensed.

FIG. 16C shows a magnified view of the location of peeler pin 1012 within cassette 900. In this preferred embodiment, peeler pin 1012 is positioned proximate to supply spool 802 in such a manner that causes a change in direction of backing member 806 around peeler pin 1012 as backing member 806 migrates from supply spool 802 to tape spool 818. This change in direction (caused by the location of peeler pin 1012) results in a partial separation of disposable instrument cover/probe cover from backing member 806.

Figure 17A:
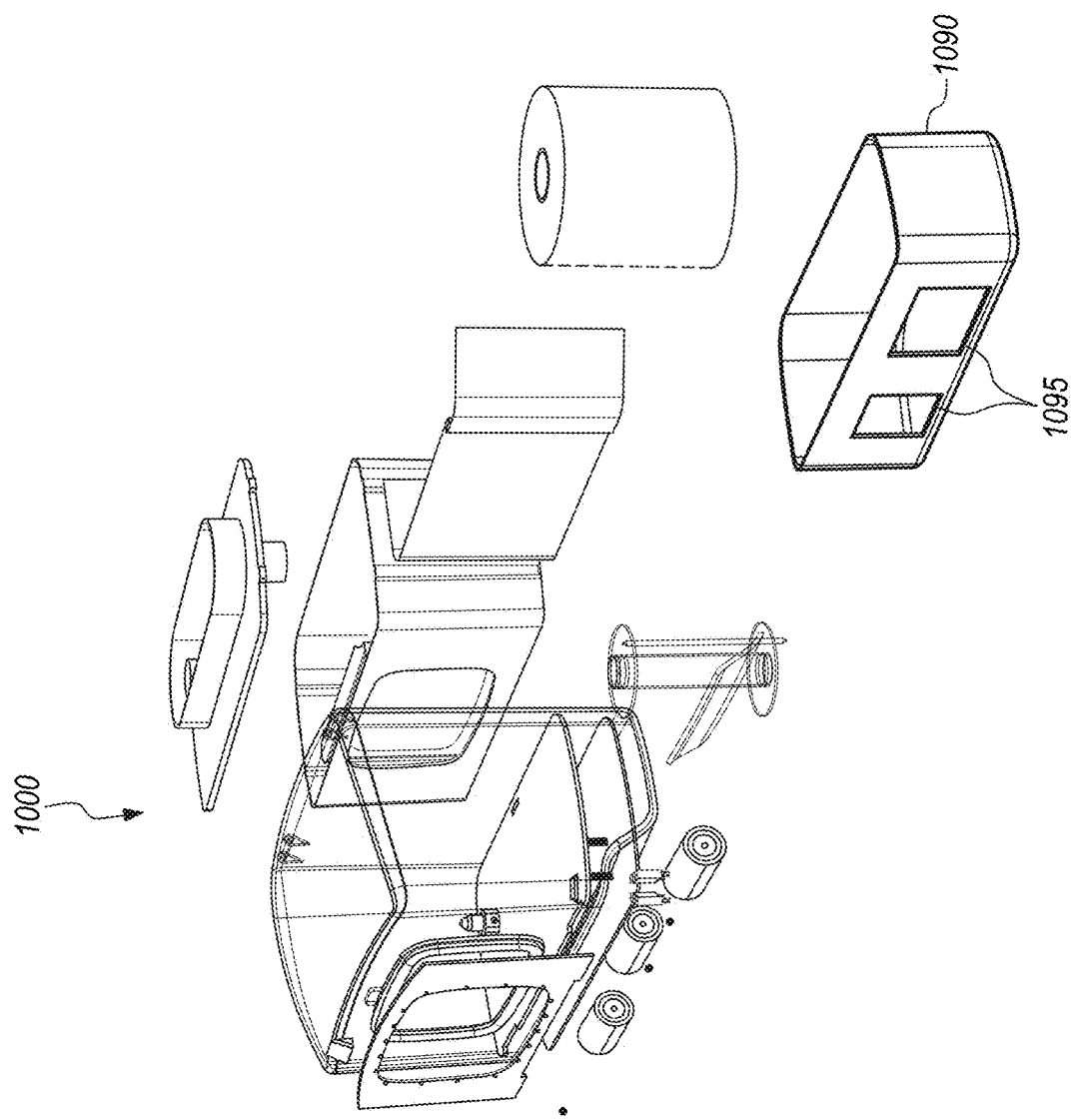
FIG. 17 shows an exploded view (17A) and a perspective view as assembled (17B) of the preferred embodiment of the ultrasound probe cover dispenser, with barrier wrapper, of the present invention.

FIG. 17A shows an exploded view an exploded view of another preferred embodiment of the present invention. Probe kit 1000 is comprised of cassette 900 and housing assembly 950. Barrier wrapper 1090 is attached to the underside of housing assembly 950 and comprises wrapper windows 1095 to allow for probe covers to be more solidly affixed to probe after rolling application.

Figure 17B:
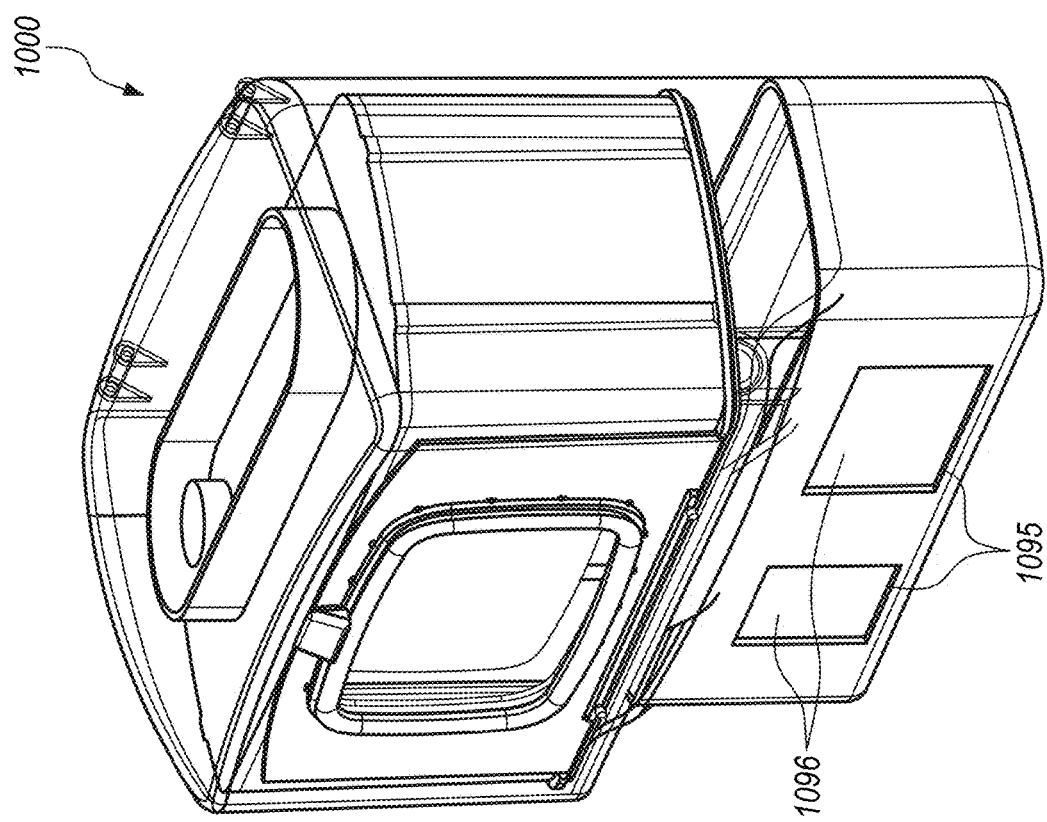

FIG. 17B shows a perspective view of a fully assembled housing assembly 950 with cassette 900 and barrier wrapper 1090. Foam inserts 1096 are observed through the wrapper windows 1095.

Figure 18:
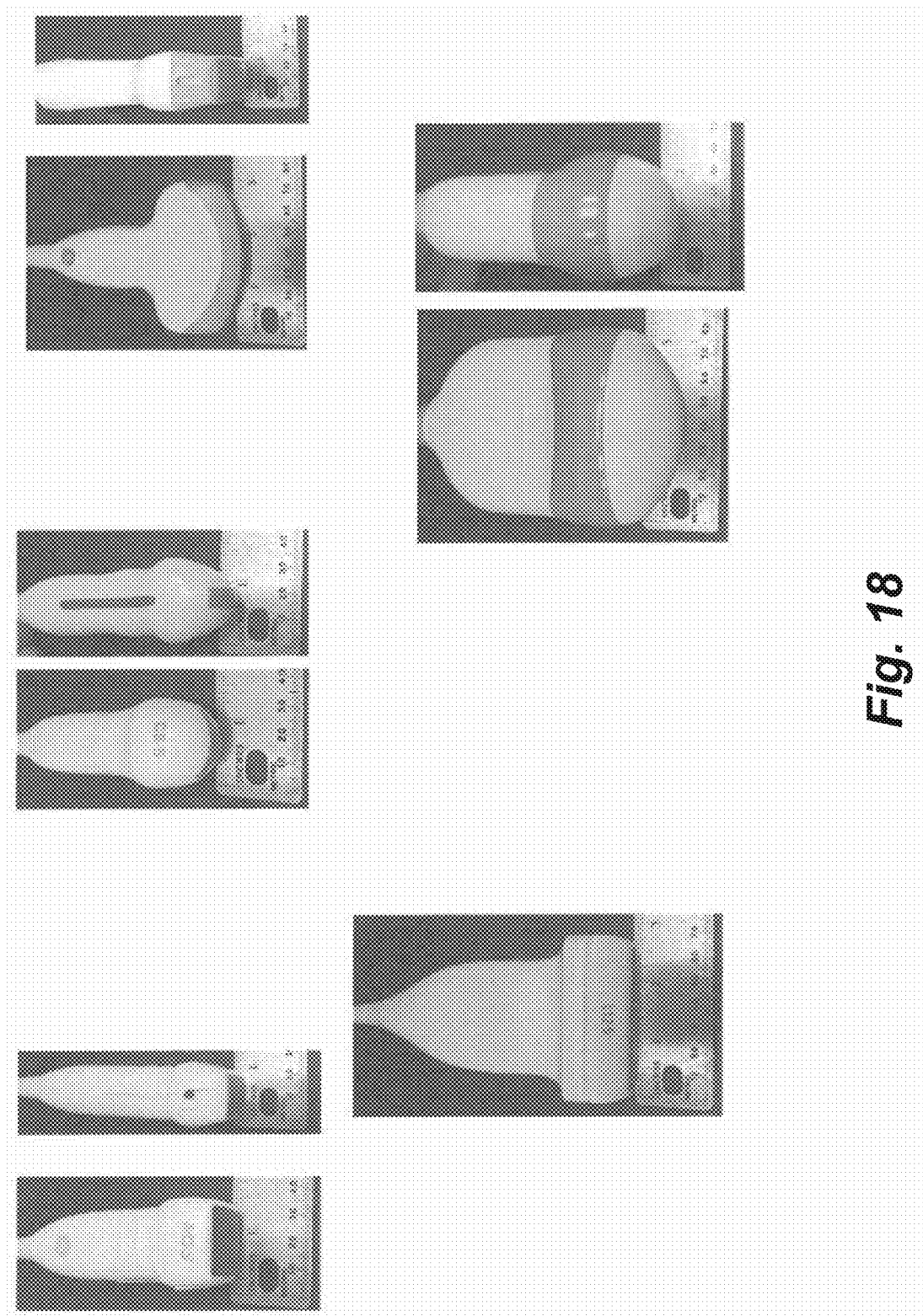
FIG. 18 shows a variety of ultrasound probes for use with the ultrasound probe cover dispenser of the present invention. Relative scales of each probe are displayed, in inches.

Preferred embodiments of ultrasound probes for use in the instant invention are shown at FIG. 18. Sizes (in inches) are also displayed for scale.

While various illustrative embodiments of the invention are described above, it will be apparent to one skilled in the art that various changes and modifications may be made therein without departing from the invention. Certain terms throughout this specification shall be considered synonyms, including but not limited to, cassette being construed as the same meaning as cartridge, for example. The appended claims are intended to cover all such changes and modifications that fall within the true scope of the invention.

What is claimed is:

1. A cassette for automatic touch-free dispensing of disposable instrument covers onto an instrument, the cassette comprising:
  a supply spool configured to hold a backing member having the disposable instrument covers disposed thereon;
  a tape spool configured to hold spent backing member without the disposable instrument covers disposed thereon, the tape spool spaced apart from the supply spool to define a flat area of the backing member disposed between the supply and tape spools, wherein the flat area further comprises a resistance section, the resistance section comprising a parallel section attached directly to the cartridge by way of perpendicular edges, thereby forming a space between the backing member and the resistance section; and
  a peeler pin positioned proximate to the supply spool to change direction of a path of the backing member to partially separate the disposable instrument covers from the backing member to ease the transfer of the disposable instrument cover onto the instrument,
  wherein the supply and tape spools are configured to rotate such that the disposable instrument covers are exposed through a cassette window positioned at a front face of the cassette, wherein the cassette comprises a lid and separate spool structures to interface with the supply spool and the tape spool within the cassette.

2. The cassette of claim 1, wherein the flat area comprises a resistance section which provides resistance to the backing member once the instrument contacts the disposable instrument cover through the cassette window.

3. The cassette of claim 1, wherein the instrument is an ultrasound probe.

4. The cassette of claim 1, wherein the cassette comprises a cassette flooring through which at least a drive port and a supply port are positioned.

5. The cassette of claim 4, wherein a drive gear connected to a motor extends through the cassette flooring at the drive port to interface with the supply spool or the tape spool.

6. The cassette of claim 4, wherein the drive port is positioned below the tape spool and the supply port is positioned below the supply spool.

7. The cassette of claim 1, wherein the flat area is sized to allow contact between an instrument and the disposable instrument covers.

8. A kit comprising a dispenser and a cassette for automatic touch-free dispensing of disposable instrument covers onto an instrument, the cassette comprising:
  a supply spool configured to hold a backing member having the disposable instrument covers disposed thereon;
  a tape spool configured to hold spent backing member without the disposable instrument covers disposed thereon, the tape spool spaced apart from the supply spool to define a flat area of the backing member disposed between the supply and tape spools, wherein the flat area further comprises a resistance section, the resistance section comprising a parallel section attached directly to the cartridge by way of perpendicular edges, thereby forming a space between the backing member and the resistance section, wherein the supply and tape spools are configured to rotate such that the disposable instrument covers are exposed through a cassette window positioned at a front face of the cassette;
  a peeler pin positioned proximate to the supply spool to change direction of a path of the backing member to partially separate the disposable instrument covers from the backing member to ease the transfer of the disposable instrument cover onto the instrument; and
  a dispenser housing with a lid configured to house the cassette, the dispenser housing comprising an access window configured to permit insertion of the instrument therethrough to permit coupling of the instrument to the disposable instrument cover exposed at the access window and positioned at the flat area of the backing member,
  wherein the supply and tape spools are configured to rotate such that the disposable instrument covers are exposed through the access window, wherein the cassette comprises a lid and separate spool structures to interface with the supply spool and the tape spool within the cassette.

9. The kit of claim 8, wherein the instrument is an ultrasound probe and the disposable instrument covers are disposable covers for application to the ultrasound probe.

10. The kit of claim 8, wherein the flat area comprises a resistance section which provides resistance to the backing member once the instrument contacts the disposable instrument cover through the cassette window.

11. The kit of claim 8, wherein the cassette window of the cassette and the access window of the dispenser housing are aligned.

12. The kit of claim 8, wherein the flat area is sized to allow contact between an instrument and the disposable instrument covers.

13. The kit of claim 8, wherein the cassette comprises a cassette flooring through which at least a drive port and a supply port are positioned.

14. The kit of claim 13, wherein a drive gear connected to a motor extends through the cassette flooring at the drive port to interface with the supply spool or the tape spool.

15. The kit of claim 13, wherein the drive port is positioned below the tape spool and the supply port is positioned below the supply spool.

* * * * *